United States Patent
Tan et al.

(10) Patent No.: US 8,586,109 B2
(45) Date of Patent: Nov. 19, 2013

(54) ANNATTO EXTRACT COMPOSITIONS INCLUDING TOCOTRIENOLS AND TOCOPHEROLS AND METHODS OF USE

(75) Inventors: Barrie Tan, Amherst, MA (US); Jose Llobrera, Belchertown, MA (US)

(73) Assignee: American River Nutrition, Inc., Hadley, MA (US)

( * ) Notice: Subject to any disclaimer, the term of this patent is extended or adjusted under 35 U.S.C. 154(b) by 817 days.

(21) Appl. No.: 12/168,819

(22) Filed: Jul. 7, 2008

(65) Prior Publication Data

US 2009/0041870 A1    Feb. 12, 2009

Related U.S. Application Data

(63) Continuation-in-part of application No. 10/823,043, filed on Apr. 12, 2004, now abandoned.

(60) Provisional application No. 60/488,310, filed on Jul. 18, 2003, provisional application No. 60/461,932, filed on Apr. 10, 2003.

(51) Int. Cl.
*A61K 36/185* (2006.01)

(52) U.S. Cl.
USPC ........... 424/727; 424/725; 424/764; 424/776; 424/750; 424/757

(58) Field of Classification Search
None
See application file for complete search history.

(56) References Cited

U.S. PATENT DOCUMENTS 5,157,132 A * 10/1992 Tan et al. ............ 549/413
6,350,453 B1 * 2/2002 Tan et al. ............ 424/776

FOREIGN PATENT DOCUMENTS

WO    03/013275 A1    2/2003

OTHER PUBLICATIONS

Frega et al., Identification and Estimation of Tocotrienols in the Annatto Liquid Fraction by Gas Chromatography-Mass Spectrum, 1998, JAOCS, 75: 1723-1727.*
Murray, 2003, http://www.lifeextensionvitamins.com/de21cevie.html.*
Pearce et al., Hypocholesterolemic Activity of Synthetic and Natural Tocotrienols, 1992, J Med Chem, 35: 3595-3606.*
Office Action, dated May 24, 2011, Canadian Intellectual Property Office.
Morrision, Errol Y. St. A; West, Manley E., The effect of *Bixa orrellana* (annatto) on blood sugar levels in the anaesthetized dog, West Indian med. j; 34(1):38-42, Mar. 1985.
WM Wan Nazaimoon and BAK Khalid, Tocotrienols-rich diet decreases advanced glycosylation end-products in non-diabetic rats and improves glycemic control in streptozotocin-induced diabetic rats, vol. 24, No. 2 Dec. 2002, 77-82.
Canadian Office Action dated Aug. 20, 2013 corresponding to Application No. 2,521,020.

* cited by examiner

*Primary Examiner* — Terry McKelvey
*Assistant Examiner* — Catheryne Chen
(74) *Attorney, Agent, or Firm* — Hogan Lovells US LLP

(57) ABSTRACT

Compositions and methods of use of annatto extracts [350-450 Dalton molecular weight fraction] including tocotrienols and tocopherols with an appropriate spectrum. This spectrum includes but not limited to low alpha tocopherol, high delta- and gamma-tocols, and mixtures with other extracts [350-450 Dalton molecular weight fraction] like palm and rice and/or nutrients.

15 Claims, 3 Drawing Sheets

TOCOPHEROL

TOCOTRIENOL

| Methyl Group Position(s) | Tocopherol | Tocotrienol |
|---|---|---|
| 5,7,8 - Trimethyl | alpha-T1 | alpha-T3 |
| 5,8 - Dimethyl | beta-T1 | beta-T3 |
| 7,8 - Dimethyl | gamma-T1 | gamma-T3 |
| 8 - Monomethyl | delta-T1 | delta-T3 |

ANNATTO EXTRACT COMPOSITIONS INCLUDING TOCOTRIENOLS AND TOCOPHEROLS AND METHODS OF USE

RELATED APPLICATIONS

This application is a Continuation-in-Part of U.S. Nonprovisional application Ser. No. 10/823,043 filed on Apr. 12, 2004 (pending), which claims priority upon U.S. provisional application Ser. No. 60/461,932 filed on Apr. 10, 2003 and claims priority upon U.S. provisional application Ser. No. 60/488,310 filed on Jul. 18, 2003, the contents of which are all herein incorporated by this reference in their entireties.

All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

OTHER REFERENCES

Ahn, K. S., et al. (2007). "Gamma-Tocotrienol Inhibits Nuclear Factor-kappaB Signaling Pathway through Inhibition of Receptor-interacting Protein and TAK1 Leading to Suppression of Antiapoptotic Gene Products and Potentiation of Apoptosis." J. Biol. Chem. 282(1):809-820.

Anderson, S., J. Qiu, et al. (2003). "Tocotrienols induce IKBKAP expression: a possible therapy for familial dysautonomia." Biochem Biophys Res Commun. 306(1): 303-309.

Araki, Y., et al. (2003). "Human monocyte chemotaxis is induced by glycolaldehyde-derived pyridine (GA-pyridine), one of structures identified from AGE-modified proteins." Diabetes 52(Suppl. 1): A172 extended abstract. 738P.

Cahoon, E., S. Hall, et al. (2003). "Metabolic redesign of vitamin E biosynthesis in plants for tocotrienol production and increased antioxidant content." Nat Biotechnol. 21(9): 1082-1087.

Carr, A. and B. Frei (2000). "The Role Of Natural Antioxidants In Preserving The Biological Activity Of Endothelium-Derived Nitric Oxide." Free Rad. Biol. Med. 28(12): 1806-1814.

Chao, J. (2002). "Inhibitory Effect of d-Tocotrienol, a HMG CoA Reductase Inhibitor, on Monocyte-Endothelial Cell Adhesion." J. Nutr. Sci. Vitaminol. 48: 332-337.

Chen, Y. D. and G. M. Reaven (1998). "Insulin Resistance and Atherosclerosis." Ann. Rev. Diabetes: 105-116.

Colwell, J. (1997). "Aspirin therapy in diabetes." Diabetes Care 20: 1767-1771.

Colwell, J. (2004). "Aspirin therapy in diabetes." Diabetes Care 27(Supp. 1): S72-S73.

Deepa, R., S. Pillarisetti, et al. (2003). "Elevation of Serum VCAM-1, IL-6, MCP-1 and CRP in Insulin Resistant Prediabetic and Diabetic Asian South Indian Subjects." Diabetes 52(Suppl. 1): A153 extended abstract. 658P.

DeFronzo, R. A. (1998). "Pathogenesis of Type 2 Diabetes: Metabolic & Molecular Implications for Identifying Diabetes Genes." Ann. Rev. Diabetes: 1-93.

Dormann, P. (2003). "Corn with enhanced antioxidant potential." Nat Biotechnol. 21(9): 1015-1016.

Elson, C. E. (1995). "Suppression of Melvalonate Pathway Activities by Dietary Isoprenoids: Protective Roles in Cancer and Cardiovascular Disease." J. Nutr. 125: 1666S-1672S.

Fairus, S., et al. (2003). "Palm Tocotrienols: Tracing its Metabolism and Biokinetics." Prodeedings of PIPOC Food Tech. Nutri.: 236-246.

Farrell, P. and J. Bieri (1975). "Megavitamin E Supplementation in Man." Am. J. Clin. Nutr. 28: 1381-1386.

Festa, A., A. J. Hanley, et al. (2003). "Inflammation in the Prediabetic State Is Related to Increased Insulin Resistance Rather Than Decreased Insulin Secretion." Circulation 108 (15): 1822-1830.

Goldstein, J. L. and M. S. Brown (1990). "Regulation of the Mevalonate Pathway." Nature 343:425-430.

Gu, J., et. al (1997). "Combined Effects of Sesamin with Alpha T1 or T3s on Lipid and Immune Indices in Brown-Norway Rats." Nutr. Res. 17: 339-350.

Guillet-Deniau, I., et al. (2003). "Glucose induces de novo fatty acid synthesis in rat skeletal muscle through a SREBP-1c dependent pathway." Diabetes 52(Suppl. 1): extended abstract. 1024P.

Guthrie, N., A. Gapor, et al. (1997). "Inhibition of Proliferation of Estrogen Receptor-negative MDA-MB-435 and -positive MCF-7 Human Breast Cancer Cells by Palm Oil Tocotrienols and Tamoxifen, Alone and in Combination." J. Nutr. 127(3): 544S-548S.

Hayes, K., A. Pronczuk, et al. (1993). "Differences in the plasma transport and tissue concentrations of tocopherols and tocotrienols: observations in humans and hamsters." Proc Soc Exp Biol Med. 202(3): 353-359.

Igarashi, O., et al. (2003). "Diuretics containing gamma-tocotrienol, US Patent Application Pub No.: US 2003/0139467 A1. Pub. Date: Jul. 24, 2003.".

Ikeda, S., T. Tohyama, et al. (2003). "Dietary alpha-tocopherol decreases alpha-tocotrienol but not gamma-tocotrienol concentration in rats." J, Nutr. 133(2): 428-434.

Ima-Nirwana, S., et. al. (2000). "Palm vitamin E prevents osteoporosis in orchidectomized growing male rats." Nat. Prod. Sci. 6: 155-160.

Jaleel, A., et al. (2003). "Identificaiton of amadori modified proteins by western blot and mass spectrometry in plasma of type-2 diabetes patients." Diabetes 52(Suppl. 1): A157 extended abstract. 675P.

Jenkins, A. J. and T. J. Lyons (2000). "Preventing Vascular Disease in Diabetes." Practical Diabetology 19: 19-34.

Jiang, Q., S. Christen, et al. (2001). "Gamma-Tocopherol, the Major Form of Vitamin E in the US Diet, Deserves More Attention." Am. J. Clin. Nutr. 74: 714-722.

Kaku, S., S. Yunoki, et al. (1999). "Effect of dietary antioxidants on serum lipid contents and immunoglobulin productivity of lymphocytes in Sprague-Dawley rats." Biosci Biotechnol Biochem. 63(3): 575-576.

Kamat, J., et al. (1997). "Tocotrienols from Palm Oil as Effective Inhibitors of Protein Oxidation and Lipid Peroxidation in Rat Liver Microsomes." Molecular and Cellular Biochemistry 170: 131-138.

Kamat, J. and T. Devasagayam (1995). "Tocotrienols from palm oil as potent inhibitors of lipid peroxidation and protein oxidation in rat brain mitochondria." Neurosci Lett. 195(3): 179-182.

Khor, H. and T. Ng (2000). "Effects of Administration of a-Tocopherol and Tocotrienols on Serum lipids and Liver HMG CoA Reductase Activity." Int. J. of Food Sci. and Nutr. 51: S3-S11.

Kooyenga, D., T. Watkins, et al. (2001). Antioxidants Modulate the Course of Carotid Atherosclerosis: A Four-year Study. Micronutrients and Health. Molecular Biological Mechanisms. K. Nesaretnam and L. Packer, AOCS Press: 366-375.

Kraegen, E. (1998). "Physiologic manifestations of PPAR-gamma activation: preclinical studies." Clinical Courier 16(48): 5-7.

Lehmann, J. (1981). "Comparative Sensitivities of Tocopherol Levels of Platelets, Red Blood Cells, and Plasma for Estimating Vitamin E Nutritional Status in the Rat." Am J. Clin. Nutr. 34: 2104-2110.

Liao, J. K. (1998). "Endothelium and Acute Coronary Syndromes." Clin Chem. 44: 1799-1808.

Liu, M., R. Wallin, et al. (2002). "Mixed Tocopherols Have a Stronger Inhibitory Effect on Lipid Peroxidation Than a-Tocopherol Alone." J. Cardiovasc. Pharmacol. 39(5): 714-721.

McIntyre, B., K. Briski, et al. (2000). "Antiproliferative and Apoptotic Effects of Tocopherols and Tocotrienols on Preneoplastic and Neoplastic Mouse Mammary Epithelial Cells." P.S.E.B.M 224: 292-301.

McLaughlin, T., et al. (2003). "Prediction of IR with plasma TG or TG/HDL ratio." Diabetes 52(Suppl. 1): A224 extended abstract. 962P.

Meigs, J., F. Hu, et al. (2003). "Endothelial Dysfunction Predicts Development of Type 2 Diabetes." Diabetes 52(Suppl. 1): A58 extended abstract. 249-OR.

Mensink, R., A. Houwelingen, et al. (1999). "A Vitamin E Concentrate Rich in Tocotrienols Had No Effect on Serum Lipids, Lipoproteins, or Platelet Function in Men With Mildly Elevated Serum Lipid Concentrations." Amer. J. Clin. Nutr. 69(2): 213-219.

Mezey, E., A. Parmalee, et al. (2003). "Of splice and men: what does the distribution of IKAP mRNA in the rat tell us about the pathogenesis of familial dysautonomia?" Brain Res. 983(1-2): 209-214.

Mustad, V., C. Smith, et al. (2002). "Supplementation With 3 Compositionally Different Tocotrienol Supplements Does Not Improve Cardiovascular Disease Risk Factors in Men and Women With Hypercholesterolemia." Am. J. Clin. Nutr. 76(6): 1237-1243.

Nazaimoon, W. and B. Khalid (2002). "Tocotrienol-rich diet decreases AGE in non-diabetic rats and improves glycemic control in streptozotocin-induced diabetic rats." Malay. J. Pathol. 24: 77-82.

Newaz, M. and N. Nawal (1999). "Effect of gamma-tocotrienol on blood pressure, lipid peroxidation and total antioxidant status in spontaneously hypertensive rats." Clin. Exper. Hypertension 21: 1297-1313.

Newaz, M., Z. Yousefipour, et al. (2003). "Nitric oxide synthase activity in blood vessels of spontaneously hypertensive rats: antioxidant protection by gamma-tocotrienol." J Physiol Pharmacol. 54(3): 319-327.

Norazlina, M., et al. (2002). "Tocotrienols are Needed for Normal Bone Calcification of Growing Female Rats." Asia Pacific J. Clin. Nutr.: 194-199.

Norazlina, M., et al. (2007). "Effects of vitamin E supplementation on bone metabolism in nicotine-treated rats." Singapore Med. J. 48(3): 195-199.

Packer, L., S. Weber, et al. (2001). "Molecular aspects of alpha-tocotrienol antioxidant action and cell signalling." J. Nutr. 131(2): 369S-73S.

Pearce, B., R. Parker, et al. (1992). "Hypocholesterolemic activity of synthetic and natural tocotrienols." J Med Chem. 35(20): 3595-3606.

Prescott, S. M., T. M. Mcintyre, et al. (2001). "Events at the Vascular Wall: The Molecular Basis of Inflammation." J. Invest. Med. 49: 104-111.

Qureshi, A., et al. (2001). "Novel Tocotrienols of Rice Bran Inhibit Atherosclerotic Lesions in C57BL/6 ApoE-deficient Mice." J. Nutr. 131: 1-13.

Qureshi, A., et al. (2002). "Effects of Stabilized Rice Bran, Its soluble and Fiber Fractions on Blood Glucose Levels and Serum Lipid Parameters in Humans with Diabetes Mellitus Type I and II." J. Nutritional Biochemistry 13: 175-187.

Qureshi, A., E. Bradlow, et al. (1997). "Novel Tocotrienols of Rice Bran Modulate Cardiovascular Disease Risk Parameters of Hypercholesterolemic Humans." J. Nutritional Biochemistry 8: 290-298.

Qureshi, A., B. Pearce, et al. (1996). "Dietary a-Tocopherol Attenuates the Impacet of g-Tocotrienol on Hepatic 3-Hydroxy-3-Methylglutaryl Coenzyme A Reductase Activity in Chickens." J. Nutr. 126: 389-394.

Qureshi, A. and D. Peterson (2001). "The combined Effects of Novel Tocotrienols and Lovastatin on Lipid Metabolism in Chickens." Atherosclerosis 156: 39-47.

Qureshi, A., B. Bradlow, et al. (1995). "Response of Hypercholesterolemic Subjects To Administration of Tocotrienols." Lipids 30: 1171-1177.

Rekeneire, N., R. Peila, et al. (2003). "Inflammation, Insulin, Glucose In Non Diabetic Older Persons. (Epidemiology)." Diabetes 52(Suppl. 1): A218 extended abstract. 937P.

Ridker, P., J. Buring, et al. (2003). "C-Reactive Protein, the Metabolic Syndrome, and Risk of Incident Cardiovascular Events: An 8-Year Follow-Up of 14,719 Initially Healthy American Women." Circulation 107(3): 391-397.

Robbesyn, F., V. Garcia, et al. (2003). "HDL Counterbalance the Proinflammatory Effect of Oxidized LDL By Inhibiting Intracellular Reactive Oxygen Species Rise, Proteasome Activation, and Subsequent Nf-Kappab Activation in Smooth Muscle Cells." FASEB J. 17(6): 743-745.

Saldeen, T., D. Li, et al. (1999). "Differential effects of alpha- and gamma-tocopherol on low-density lipoprotein oxidation, superoxide activity, platelet aggregation and arterial thrombogenesis." J Am Coll Cardiol. 34(4): 1208-1215.

Schalkwijk, C., et al. (2003). "Increased accumulation of the glyoxidation product N (carboxymethyl) lysine in hearts of diabetic patients." Diabetes 52(Suppl. 1): A165 extended abstract. 709P.

Sen, C., et al. (2000). "Tocotrienol Potently Inhibits Glutamate-induced pp 60c-Src Kinase Activation and Death of HT4 Neuronal Cells." J. Biological Chemistry 275: 13049-13055.

Serbinova, E., V. Kagan, et al. (1991). "Free Radical Recycling and Intramembrane Mobility in the Antioxidant Properties of Alpha-Tocopherol and Alpha-Tocotrienol." Free Rad. Biol. Med. 10: 263-275.

Sheppard, A. J., J. Pennington, et al. (1993). Analysis and Distribution of Vitamin E in Vegetable Oils and Foods. Vitamin E in Health and Disease. L. Packer and J. Fuchs, Marcel Dekker, Inc.: 9-31.

Shi, H., N. Noguchi, et al. (1999). "Formation of phospholipid hydroperoxides and its inhibition by alpha-tocopherol in rat brain synaptosomes induced by peroxynitrite." Biochem Biophys Res Commun. 257(3): 651-656.

Smith, S. (1998). "The molecular pharmacology of PPAR-gamma." Clinical Courier 16(48): 3-4.

Sylvester, P. and A. Theriault (2003). "Role of Tocotrienols in the Prevention of Cardiovascular Disease and Breast Cancer." Current Topics in Nutraceutical Research 1(2): 121-136.

Szwergold, B., et al. (2003). "Intracellular nonenzymatic glycation of hemoglobin in human erythrocytes is controlled by enzymatic deglycation mechanisms." Diabetes 52(Suppl. 1): A190 extended abstract. 815P.

Tan, B. (1992). "Antitumor Effects of Palm Carotenes and Tocotrienols in HRS/J Hairless Female Mice." Nutrition Research 12: S163-S173.

Theriault, A., et al (1999). "Tocotrienol: A Review of its Therapeutic Potential." Clinical Biochemistry 32(July): 309-319.

Tomeo, A., et al. (1995). "Antioxidant Effects of Tocotrienols in Patients with Hyperlipidemia and Carotid Stenosis." Lipids 30: 1179-1183.

Traber, M., et al. (1997). "Diet-derived and topically applied tocotrienols accumulate in skin and protect the tissue against ultraviolet light-induced oxidative stress." Asia Pacific J. Clin. Nutri. 6: 63-67.

Traber, M., et al. (1998). "Penetration and distribution of alpha-tocopherol, alpha- or gamma-tocotrienols applied individually onto murine skin." Lipids 33: 87-91.

Tsai, A., J. Kelly, et al. (1978). "Study on the Effect of Mega-Vitamin E Supplementation in Man." Am. J. Clin. Nutr. 31: 831-837.

Wallace, A., D. Chinn, et al. (2003). "Taking simvastatin in the morning compared with in the evening: randomised controlled trial." BMJ 327(7418): 788.

Watkins, T., M. Geller, et al. (1999). "Hypocholesterolemic and antioxidant effect of rice bran oil non-saponifiables in hypercholesterolemic subjects." Environmental & Nutritional Interactions 3: 115-122.

Watkins, T., M. Bierenbaum, et al. (1999). Tocotrienols: biological and health benefits. Antioxidant Status, Diet, Nutrition, and Health. A. M. Papas, CRC Press: 479-496.

Weber, C., et al. (1997). "Efficacy of Topically Applied Tocopherols and Tocotrienols in Protection of Murine Skin from Oxidative Damage Induced by UV-Irradiation." Free Radical Biology and Medicine. 22: 761-769.

Yap, S., K. Yuen, et al. (2001). "Pharmacokinetics and bioavailability of alpha-, gamma- and delta-tocotrienols under different food status." J. Pharm. Pharmacol. 53(1): 67-71.

Yoshida, Y., et al. (2003). "Comparative Study on the Action of Tocopherols and Tocotrienols as Antioxidant: Chemical and Physical Effects." Chemistry and Physics of Lipids 123: 63-75.

Yu, W., M. Simmons-Menchana, et al. (1999). "Induction of Apoptosis in Human Breast Cancer Cells by Tocopherols and Tocotrienols." Nutrition and Cancer 33: 26-32.

BACKGROUND OF THE INVENTION

1. Field of the Invention

The invention is on the compositions and uses of the extract [350-450 Dalton molecular weight fraction] from the annatto seed and such extract that is annatto oil or oleoresin containing non-saponifiables, especially non-saponifiable terpenoids.

2. Description of the Related Art

Tocotrienols generally are classified as farnesylated chromanols (FC) and mixed terpenoids. Tocopherol and tocotrienol are believed to have beneficial effects because they act as antioxidants. Tocotrienols, in particular, have been documented to possess hypocholesterolemic effects, as well as, an ability to reduce atherogenic apolipoprotein B and lipoprotein plasma levels. Further, tocotrienols are believed to be useful in the treatment of cardiovascular disease and cancer (Theriault, A., et al., 1999; Watkins, T. et al., 1999). Delta-tocotrienol and gamma-tocotrienol, in particular, have been identified as effective suppressants of cholesterol activity (Qureshi, A., et al., 1995), and in inducing apoptosis of breast cancer cells (Yu, W. et al., 1999).

Tocols, which includes tocopherols and tocotrienols, have several sources, including several vegetable oils, such as rice bran, soybean, corn and palm. However, each source of tocotrienols and tocopherols generally contains more than a single tocol homolog. For example, palm oil and rice bran oil generally include both tocotrienols and tocopherols. Further, alpha-tocopherol has been reported to attenuate certain effects of tocotrienols, such as the cholesterol-suppressive activity of gamma-tocotrienol (Qureshi, A., et al., supra.). In addition, because of their structural similarity, tocotrienols and tocopherols can be difficult to separate.

Tocotrienols (including delta- and gamma-tocotrienols) and geranyl geraniols have been discovered in the seeds of *Bixa orellana* Linn, otherwise known as the achiote tree. It is a member of the Bixaceae family and is native to tropical America. It is grown commercially in other parts of the world, generally within 20° of the equator or more preferably within 15° of the equator.

The seeds of *Bixa orellana* are the source of a reddish-orange colorant, known as annatto, that contains bixin and orelline, both of which are carotenoid pigments. The colorant is used commonly in foods, dyes and polishes. Typically, annatto is extracted from dehusked seeds in an aqueous caustic solution. The colorant is precipitated from the aqueous solution by addition of acid, and the precipitated colorant is removed by filtration. The oily phase is usually separated from the aqueous solution, and discarded as a byproducts.

A "byproduct solution of *Bixa orellana* seed components" is defined herein as a solution derived from *Bixa orellana* seed components having a concentration of annatto colorant significantly reduced from that of *Bixa orellana* seeds themselves. Other common terms for byproduct solution used for commercial products include: oil-soluble annatto color, annatto oil, annatto oleoresin, or annatto extract.

Annatto extracts contain predominantly tocotrienols, geranyl geraniols, bixins and to a lesser extent components of oleoresinous materials, of which all these major and minor components (both saponifiables and non-saponifiables) are unique to annatto extracts. These extracts can be used as a nutritional supplement, nutraceutical, functional food and beverage, animal ingredient and pharmaceutical, or as an admixture with other natural extracts [350-450 Dalton molecular weight fraction] or nutrients.

Vitamin E constitutes a class of tocochromanols containing at least four tocopherols and at least four tocotrienols. "Toco" means birth, "pheren" to bring forth, "triene" three double bonds, "ol" alcohol, and "chroman" the attached ring structure. The chroman alcohol has consistently indicated that all E vitamers are powerful membrane-soluble antioxidants (Serbinova, E., et al., 1991; Yoshida, Y., et al., 2003). The "triene" refers to the 3 double-bonded tail in a tocotrienol which differentiates it from a tocopherol's saturated tail. The "triene" tail (also referred to as farnesyl tail) is about a third shorter than the saturated tail (also referred to as phytyl tail). These vitamin E tocochromanols include the lesser abundant tocodienols ("diene" with two double-bonded tail) and tocomonoenols ("monoene" with one double-bonded tail). The Greek alphabets "alpha", "beta", "gamma" and "delta" refer to the degree of methyl substitutions in the chroman structure (Table 1).

TABLE 1

| | Molecular weights | |
|---|---|---|
| | Tocopherol | Tocotrienol |
| Alpha | 430 | 424 |
| Beta | 417 | 411 |
| Gamma | 417 | 410 |
| Delta | 403 | 396 |

Vitamin E, including tocopherols and tocotrienols, are typically 390-430 Daltons in molecular weight or more broadly 350-450 Daltons in molecular weight, which includes tocopherols and tocotrienols without any methylated groups in the lower range and tocopherols and tocotrienols with fully methylated groups in the higher range.

The reason for the antioxidant scavenging efficiency of tocotrienol (T3) is because of its shorter farnesyl tail. The farnesylated tail enables the tocotrienol to move with superior mobility across cell membranes, giving rise to greater efficiency in free-radical scavenging activity (Serbinova, E. et al., 1991; Packer, L., et al., 2001). The longer phytyl tail of the tocopherol (T1), which anchors deeply into lipid membranes, renders tocopherol less mobile and thereby making it less efficient as a scavenger than T3.

The farnesol tail is required to reduce cholesterol. Farnesol down regulates, as well as, degrades HMG CoA reductase, the enzyme that controls cholesterol biosynthesis. It is believed that the farnesyl tail of tocotrienol works by this mechanism (Pearce, B., et al., 1992), a possibility that does not exist with tocopherol. Fully occupied methyl substitution on the chromanol (e.g., alpha isomer) prohibits any reaction and unoccupied substitution on the ring (e.g., delta isomer) makes available reactive nitrogen oxide trapping capability (Jiang, Q., et al., 2001). As shown in FIG. 2, when the carbon position 5 is unoccupied, T1 or T3 becomes "C-5 unsubstituted".

Tocotrienol contains three repeating isoprene units giving rise to the farnesyl tail. Geranyl geraniols (GG), both cis and trans isomers, contain four isoprene repeating units and surprisingly the tocotrienol farnesyl moiety is contained in the GG tail, and therefore GG is believed to be an unique component in the annatto extract, among other valuable components. In fact, the entire GG molecule is contained in and used for the biosynthesis of a tocotrienol molecule where one of the four isoprene moieties is embedded inside the T3 chroman ring (Elson, C., et al., 1995; Cahoon, E., et al., 2003; Dormann, P., 2003). See FIG. 2. Hence, both GG and tocotrienol structures have a common moiety, farnesyl group, which is believed to modulate biological activities including some overlapping activities. Annatto carotenoids (with conjugated double bonds) of various chain lengths and existing as non-oxygenated carotenes, oxygenated xanthophylls, such as free alcohols, acids, aldehydes, ketones, esterified or etherified with other annatto extract components are inclusive of the said extracts, and of this invention.

FIG. 1 shows the tocols compositions from different natural sources are highly varied, which argues for the standardization of tocols to produce an "appropriate spectrum" to address appropriate diseases and conditions, a concept that surprisingly has not been implemented. Annatto extract contains tocols that are consistent, typically 90% delta-T3 and 10% gamma-T3. The rationale for the use of tocotrienol containing annatto seed lipids is to increase the in vivo and ex vivo biological activities of these admixtures, and to increase the biological potency of these admixtures by decreasing the amount of alpha-T1 consumed. Alpha-tocopherol has been shown to interfere with tocotrienol's ability to sequester cholesterol biosynthesis (Qureshi, A., et al., 1996) and alpha-T1 has no effect on anticancer activity (Guthrie, N., et al., 1997; Yu, W., et al., 1999). Large doses of alpha-T1 has produced a marked hypertriglyceridemic effect in animals (Khor, H. and T. Ng, 2000; Lehman, J., 1981) and in humans (Farrell, P. and J. Bieri, 1975; Tsai, A. et, al., 1978). Consequently, the increase of delta-T3 and/or gamma-T3 presents superior biological and antioxidant properties vis-à-vis alpha-T1.

Table 2 shows a non-exhaustive sample of diverse health benefits and protection of the eight classically and individually known E vitamers. A need exists to develop a rationale for an "appropriate spectrum" tocols product that would normalize and/or optimize biologic functions without the crossover mitigation of tocopherols. To date, only "full spectrum" tocols (implied presence of all eight tocols) are commercially available, espousing to deliver the composite health benefits of the individualized effects of those found in Table 2. It remains unsubstantiated that full-spectrum tocols will deliver the complete effects of these individually identified properties. Therefore, these full-spectrum tocols lack a compositional, technical and/or scientific basis or rationale. Currently, no present art teaches compositions and methods of use in humans, nor teaching so efficaciously and by simply adding natural tocols extracts in appropriate combinations.

TABLE 2

Isolated uses and effects of individual tocopherols and tocotrienols.

| | |
|---|---|
| Alpha-tocopherol | High abundance in sun flower and cotton seeds. Highest Vitamin E activity, Vitamin E claims in food/supplement systems. High levels of alpha-T1 mitigate effects of tocotrienols. |
| Beta-tocopherol | Low abundance in plants (found in wheat germ). |
| Gamma-tocopherol | High abundance in soy and corn. Nitrogen dioxide scavenging (smoking detoxification), natriuretic. High levels of alpha-T1 inhibit gamma-T1 absorption |
| Delta-tocopherol | Abundance in soy and wheat germ. Both delta-T1 and gamma-T1 are antioxidants in food systems (as mixed tocopherols in preserving foods), both trap RNOS |
| Alpha-tocotrienol | Abundance in rice and palm. Powerful anti-oxidant compared to alpha-T1 (40-60X in some biologic systems). First discovered to reduce cholesterol, but is a weak reducer. Inhibits neurotoxicity; cell signaling; skin deposition. |
| Beta-tocotrienol | Low abundance in plants (found in wheat germ). Not a significant biologic contributor with effect same as alpha-T3 or unknown. |
| Gamma-tocotrienol | High abundance in rice, palm, and annatto. Natriuretic and inhibits cancer, atherosclerosis, osteoporosis, cholesterol, and hypertension. |
| Delta-tocotrienol | High abundance in annatto. The most active component among tocotrienols. Biologic activity: 1-2 times greater than gamma-T3 and 4-10 times greater than alpha-T3. Delta-T3 repairs nerve damage and inhibits inflammatory stimuli, cholesterol, and cancer. |

It is generally desirable to target diseases with specific isomers of tocols. For example, to lower lipids, it is desirable to have the highest levels of delta-T3 and gamma-T3 and lowest levels of tocopherols, especially alpha-T1 (Qureshi, A., et al., 1996). Such compositional specificity which is required to lower cholesterol is presently unattainable. Table 3 presents the natural compositional abundance typically found in plant sources. The natural abundance of palm and rice sources favors relatively large amounts of alpha-T3 and gamma-T3, as well as, large amounts of tocopherols. Consequently, the disclosed use of palm and rice TRFs to lower lipids has limited utility. This is because these TRFs are high in alpha-T3, low or absence in delta-T3 and high in tocopherols (30-50%), especially alpha-T1. Such compositional variability in TRF fractions have been responsible for several equivocal clinical study outcomes (Mustad, V., et al., 2002; Mensink, R., et al. 1999).

Soy and corn oils contain exclusively tocopherols, although they tend to be highest in the C5 unsubstituted tocopherols (70-90% as delta-T1 and gamma-T1) (see, Sheppard, A. et al., 1993). Such high levels of C5 unsubstituted delta-T1 and gamma-T1 from soy and corn (Table 3) have unique admixture application, which unexpectedly have not been implemented.

TABLE 3

Compositional abundance of tocotrienols in various plant source materials.

| Source of material | Tocotrienols (% wt TRF) | | | Tocopherols (% wt TRF) | | |
|---|---|---|---|---|---|---|
| | Alpha | Gamma | Delta | Alpha | Gamma | Delta |
| Annatto oil[1] | <0.1 | 10.0 | 90.0 | <0.1 | ND | ND |
| Palm oil[2] | 26.5 | 27.9 | 9.0 | 27.6 | ND | 9.0 |
| Rice bran oil[3] | 24.7 | 19.4 | 1.1 | 44.9 | 8.5 | 1.3 |
| Rice bran oil[4] | 7.0 | 40.2 | 0.7 | 32.6 | 17.6 | 2.0 |
| Wheat germ oil[5] | 0.9 | ND | ND | 47.7 | 9.3 | 9.7 |
| Soy oil[6] | ND | ND | ND | 6.6 | 70.1 | 23.4 |
| Corn oil[6] | ND | ND | ND | 15.0 | 82.5 | 2.5 |

ND, not detected
[1]DeltaGold ®, annatto derived tocotrienol concentrate, product of American River Nutrition, Inc.
[2]TRF concentrate from palm oil (Indonesian & Malaysian origin).
[3]TRF concentrate from rice bran oil (Japanese origin).
[4]TRF concentrate from rice bran oil (Thailand origin).
[5]Contains 6.5% beta-T3 and 26% beta-T1.
[6]Sheppard et al. (1993); corn may contain traces of T3.

The effectiveness of cholesterol reduction is due to the farnesylated tail of tocotrienols where the isomeric potency of delta-T3 is greater than gamma-T3, and in turn is five-fold greater than alpha-T3 (Pearce, B., et al., 1992). Furthermore, cholesterol reduction is mitigated by tocopherols, especially alpha-T1.

It is known that the structural isomeric form of tocols (either tocopherols or tocotrienols) that confers the greatest potency has no substitution in the carbon-5 (C5) position (Jiang, Q., et al., 2001; Qureshi, A., et al., 1995; McIntyre, B., et al., 2000). FIG. 2 shows that C5 unsubstituted positions are delta and gamma isomeric forms and that C5 substituted (or occupied) positions are alpha and beta isomeric forms. Hence, delta-T3 and gamma-T3 are the most active tocotrienols, and delta-T1 and gamma-T1 are the most active tocopherols. Put together, annatto extracts can be defined as tocopherol-free and have the highest potency tocotrienols that can be combined with other tocols contained in the 350-450 Dalton molecular weight fraction of natural extracts to produce an "appropriate spectrum" tocols.

Cell line studies have predicted that delta-T3 and gamma-T3 behave synergistically, and other TRFs contain a large proportion of alpha-T3 which have no synergistic role to other tocotrienols (Pearce, B., et al., 1992). However, these aspects have never been proven in clinical studies.

Insulin Resistance

The origin of diabetes is due to defects in insulin secretion and/or action. However, it is very difficult to separate over production of insulin (hyperinsulinemia, HI) from dysfunction of insulin itself (insulin resistance, IR). It has been argued that HI and IR necessarily coexist into a form of aberrant metabolic control (Chen, Y. and G. Reaven, 1998). Alternatively, it is also reasoned that the pathogenesis of diabetes initiated with an insulin secretion defect that led to insulin dysfunction (DeFronzo, R., 1998). Regardless of the etiology of IR, the pancreatic beta cell will respond to IR by increasing insulin secretion to offset the insulin action defect. This compensatory HI will down regulate insulin action further and create a circular perpetuation of IR. Thus the plasma insulin response will become progressively impaired and pancreatic beta cell exhaustion will eventuate. Because of these circular events leading to IR, overt diabetics are frequently on insulin medication. Clinically and epidemiologically, IR (a prediabetes state), and not insulin level, marks the progression to diabetes.

Insulin resistance (IR) is associated with increased risk of cardiovascular disease (CVD), Type 2 diabetes mellitus (T2DM), hypertension, polycystic ovarian syndrome (PCOS) and alcohol-unrelated fatty liver disease. However, plasma insulin measurement is not standardized across clinical laboratories, and therefore is an unreliable marker. Therefore, a surrogate marker was developed for insulin resistance, where the IR criteria are TG/HDL≥3.5 and/or TG≥140 mg/dL (McLaughlin, T., et al. 2003).

Inflammation

The process(es) of inflammation can explain numerous underlying mechanisms of cancer, degenerative disease, atherosclerosis and thrombosis (arterial clogging), and indeed global inflammation processes themselves (e.g., acute and chronic inflammation, autoimmune diseases, joint pain and rheumatoid arthritis). It is known that tocotrienols reduce certain inflammatory markers, such as, thromboxane (TXB4), prostaglandin E2 (PGE2), platelet aggregation, tumor necrosis factor (TNF) and nuclear factor kappa B (NFkB) (Qureshi, A., et al., 2002, 2001, & 1997; Qureshi, A. and D. Peterson, 2001; Watkins, T., et al., 1999; Tomeo, A., et al., 1995; Kooyenga, D. et al., 2001; Ahn et al., 2007). There is a possible role of inflammatory proteins on prediabetic condition, especially of IR. Subjects with IR had higher VCAM-1, CRP, IL-6 and TNFα (Deepa, R., et al., 2003; Rekeneire, N., et al., 2003; Festa, A., et al., 2003).

Cardiovascular Disease

Cardiovascular disease has been differentiated into low, intermediate and high risk categories (Ridker, P., et al., 2003). The study indicated that the individuals with the lowest CVD risk were subjects with the lowest CRP and without IR. Conversely, the study showed that the individuals with the highest CVD risk were subjects with the highest CRP and with IR. Put together, annatto C5 unsubstituted T3 reduce IR and CRP, and therefore reduce prediabetic conditions of IR, diabetes, and especially diabetic and non-diabetic CVD.

Cardiovascular disease and T2DM have shared common antecedents of metabolic events and processes. They are diseases of chronic dysfunction of the microvascular and macrovascular systems, and vaso-endothelial dysfunction of the endocrine system (Liao, J., 1998). Molecular processes often involve oxidative stresses, production of bioactive materials, leading to inflammation processes. For example C-reactive protein, a bioactive material, is a sensitive marker of inflammation.

Inflammation processes in the vasculature have been widely reviewed (Jenkins, A. and T. Lyons, 2000; Prescott, S., et al., 2001; Sylvester P. and A. Theriault, 2003). Gamma-tocopherol (gamma-T1) and gamma-T3 upregulate endothelial nitric oxide synthase, and these two C5 unsubstituted gamma isomers are important in preventing vascular and endothelial dysfunction (Carr, A. and B. Frei, 2000; Newaz, M., et al., 2003) and that delta-T3 followed by gamma-T3 markedly inhibit bioactive materials, namely VCAM-1 and E-selectin (Chao, J., et al., 2002). This is especially relevant because these endothelial dysfunction markers (E-selectin, ICAM-1 and VCAM-1) predict T2DM, and are independent precursors of T2DM (Meigs, J., et al., 2003). Therefore, the C5 unsubstituted tocols are uniquely suited to inhibit bioactive materials orchestrated by inflammatory stimuli and prevent the tethering of circulating monocytes and leukocytes onto endothelial cells. The break of this restraint onto the circulating cells by the C5 unsubstituted tocols is one critical intervention in protecting the integrity of the vasculature, and therefore atherosclerosis.

HDL is well known for its role in circulating cholesterol back to the liver. Moreover, the HDL particles ("good cholesterol") have anti-inflammatory and anti-thrombotic properties and suppress surface bioactive materials, as well as, markedly inhibit oxidized LDL formation and NFkB activation (Robbesyn, F., et al., 2003; Jenkins, A. and T. Lyons, 2000).

Lipidemia and Diabetic Dyslipidemia

Tocotrienols have been used for treatment of lipidemia and diabetic dyslipidemia, through tocotrienol inhibition of hepatic cholesterol biosynthesis, specifically via the inhibition of HMGR, the rate limiting step in cholesterol synthesis. However, diabetes represents a plethora of pathological events besides cholesterol dysfunction where T3 has not been represented to work, especially the C5 unsubstituted tocols. Sterol regulatory element binding protein-1 (SREBP-1) is a transcription factor that responds to nutritional status and regulates metabolic gene expression in various organs, including liver, adipose and muscle. It has been shown that insulin and glucose induced de novo fatty acid synthesis leading to a rapid increase in lipogenic flux in skeletal muscle. Such lipid accumulation is associated with muscle IR in obesity and T2DM, and is stimulated/mediated via the SREBP-1 expression (Guillet-Deniau, I., et al., 2003). As discussed earlier, IR is tightly associated with increased lipids (McLaughlin, T., et al., 2003) and increased insulin or HI (DeFronzo, R., 1998).

Diabetes

Diabetes may be considered a hypercoagulable state. Diabetic platelets are hypersensitive to platelet aggregating agents, and the vasoconstrictor TXB4 is a powerful platelet aggregator. Excess TXB4 release in diabetics has been associated with CVD in these patients. These matters have been well documented and is herein referenced in its entirety (Colwell, J., 1997 & 2004). Aspirin specifically blocks the omega-6 arachidonic acid-derived thromboxane TXB4 synthesis, which dramatically reduces platelet aggregation, and has been used as a primary and secondary strategy to prevent cardiovascular events in patients. Aspirin's major risks are gastric mucosal injury, G.I. hemorrhage and hemorrhagic stroke (Colwell, J., 1997 & 2004). It is known that gamma-T3, delta-T3 and gamma-T1 inhibit platelet aggregation, TXB4 and PGE2 (Qureshi, A., et al., 2002; Saldeen, T., et al., 1999) and that delta-T3 preferentially absorbs onto circulating human platelets (Hayes, K., et al., 1993). Gamma-T3 and gamma-T1 both metabolize in mammalian tissues to gamma-carboxyethyl hydroxy chromans ($\gamma$-CEHC), essentially the chromanol ring without the farnesyl and phytyl tails. It has been shown that their parent moieties, as well as, the $\gamma$-CEHC metabolite inhibit PGE2 and COX2 (Jiang, Q. et al., 2001) which further supports that C5 unsubstituted tocols play a role in inhibition of vasoconstriction, coagulation/clotting, and chemotaxis. Therefore, C5 unsubstituted tocols should help to reverse the hypercoagulable state of diabetes in a safe manner without side effects.

Diabetes is a disease of frank hyperglycemia and the control of sugar is always a standing goal. It is now recognized that glycation of lipids and proteins contributes to diabetic macrovascular and microvascular diseases. For example, glycoxidized LDLs increased binding to extracellular matrix, have procoagulant effects, extravasate into glomeruli, retinae and atheroma. Also glycoxidized albumin adheres to the aortic wall. According to one research study, there was an approximately 6-fold accumulation of glycoxidized N-(carboxymethyl) lysine (CML) in the hearts of diabetic patients as compared to normal subjects (Schalkwijk, C., et al., 2003). Other advanced glycation end-products (AGE) including Amadori modified proteins, all of which are sugar-mediated oxidation to proteins are herein referenced by way of examples (Jaleel, A., et al., 2003; Araki, Y., et al., 2003; Szwergold, B., et al., 2003). The measurement of glycated hemoglobin (HbA1c) in the blood is a standard marker to measure the history of sugar damage to tissues. Tocotrienols, especially gamma-T3 inhibit protein oxidation (Kamat, J., et al., 1997). Further, tocotrienols effectively prevented an increase in AGE in normal rats, and decreased blood glucose and HbA1c in diabetic rats (Nazaimoon, W. and B. Khalid, 2002).

Peroxisomal Proliferator Activated Receptor

Peroxisomal proliferator activated receptors (PPAR) are members of the nuclear receptor transcription factors. The metabolic consequences of PPAR$\gamma$ activation have been mostly researched on adipose tissue where it is largely expressed (Smith, S., 1998; Kraegen, E., 1998). The metabolic effects of thiazolidinediones (TZD) are: a) reduce hyperglycemia and hyperinsulinemia, b) lower FFA and TG levels, c) enhance IS and lower IR states, and d) use insulin to lower glucose. TZD are known PPAR$\gamma$ agonists or activators. Many of PPAR$\gamma$ activator functions are similar to PPAR$\alpha$ activator functions. PPAR$\alpha$ has been actively researched on liver tissue, especially with regards to lipid use (e.g., uptake and beta-oxidation). Even though the action sites of PPAR$\gamma$ (predominantly in adipose) and PPAR$\alpha$ (mainly in liver) are different, their activations have many overlapping clinical outcomes. Typically TZD and fibrates affect the activation of PPAR$\gamma$ and PPAR$\alpha$, respectively. Tocotrienols in this invention behave primarily like a TZD (and secondarily like a fibrate) as T3 metabolic effects match those four listed above for TZD. Surprisingly, the chromanol ring structure found in T3 is the same moiety found in troglitazone, a TZD. Put together, C5 unsubstituted T3 activate or agonize the nuclear transcription factor PPAR ($\gamma$, $\alpha$, or mixed) and thereby carry out the metabolic effects similar to those of TZDs and fibrates, in many common tissue sites (adipose, skeletal muscle, and kidney, macrophage, VSMC, endothelial cell) and different sites for PPAR$\gamma$ (heart, gut) and PPAR$\alpha$ (liver). These various PPAR expressions share more common sites than different ones. Mixed PPAR activation, besides PPAR$\gamma$ and PPAR$\alpha$, also includes PPAR$\delta$ whose expression is ubiquitous in all tissues.

Nervous System

Reversing damage to the neurons and brain, whether acute or chronic is an important health issue. Potential neuropotent nutrients have to address the issue of the blood brain barrier (BBB), over which the nutrients must cross over to enter the brain. All tocotrienols enter the brain in general, and they protect glutamate-induced neurotoxicity (Sen, C., et al., 2000). As well, these C5 unsubstituted tocols, both tocotrienols (McIntyre, B., et al., 2000) and tocopherols (Liu, M., et al., 2002) have particular bioavailability into cellular tissues. Brain cells are typically rich in PUFAs, especially the omega-3 DHA and EPA, and hence they are very susceptible to oxidation. In studies with brain mitochondrial organelles, tocotrienols and TRF effectively prevented oxidative damages to both lipids, as well as, proteins. Studies of brain mitochondria and rat microsomes indicate gamma-T3 is the most effective in oxidative protection followed by alpha-T3 and delta-T3 (Kamat, J. and T. Devasagayam, 1995; Kamat, J., et al., 1997). The gamma-T1 is mostly located in the biomembranes of brain homogenates, and it markedly inhibits lipid peroxidation in the brain (Shi, H., et al., 1999).

In an extreme form of neurodegenerative genetic disease, familial dysautonomia (FD), the development and survival of neurons (e.g. sensory, sympathetic, parasympathetic) are seriously impaired (Mezey, E., et al., 2003). Delta-T3 increases the IKBKAP gene transcription 3.5-fold, and all tocotrienols increase the IKAP transcripts and proteins (delta-T3 and gamma-T3 producing more than beta-T3 and alpha-T3) as much as 6-fold (Anderson, S., et al., 2003). None of the tocopherols have any effect.

Tocotrienols have been shown to reverse nerve damage and repair, genetic disposition, acute brain damage, glumate induced damage, chronic nerve/brain damage, Alzheimer's, Parkinson's, and Huntington's.

Statin Drugs

Statin drugs are known to decrease isoprenoid pool (IP) products, including intermediate and distal metabolites of CoQ10, dolichol, heme, protein synthesis, and cholesterol (Goldstein, J. L. and M. S. Brown, 1990).

Topical Applications

The skin is an unique site for tocotrienols for both topical and dietary tocotrienol application (Traber, M., et. al, 1998; Ikeda, S., et al., 2003). Tocotrienols protect UV-induced erythema and also prevent the loss of skin vitamin E (Weber, C., et al., 1997; Traber, M., et al., 1997).

Immune System

Dietary tocotrienols given to immunodeficient mice prolonged their survival, presumably via an immune system boost (Tan, B., 1992). Dietary tocotrienols increased immunoglobulin (IgA, IgG and IgM) in rat spleen and MLN lymphocytes where the extent was generally more marked in the T3 group than the alpha-T1 group (Gu, J., et al., 1997; Kaku, S., et al., 1999). Compositionally, C-5 unsubstituted tocotrienols, composed of delta-T3 and gamma-T3, accounted for 75% of the tocols used in these cited studies.

Bone Mineralization

It is known that tocotrienols prevent the loss of bone mineral density, and improve the bone calcium content of growing male and female, however, alpha-T1 supplementation does not improve the mineralization of bone in female rats (Ima-Nirwana, S., et al., 2000; Norazlina, M., et al., 2002; Norazlina, M., et al., 2007).

Hypertension

Gamma-T3 has been shown to prevent the development of increased blood pressure in spontaneous hypertensive rats (SHR) and that the lowest dose of 15 mg/kg feed (approximately translating to 75 mg T3/day for humans) was best in preventing hypertension (Newaz, M. and N. Nawal, 1999). Gamma-T3 is also shown to be a sodium excreting agent, as well as, increasing endothelial nitric oxide synthase (NOS) activity to treat essential hypertension (Igarashi, O., et al., 2003; Newaz, M., et al., 2003). The water-soluble metabolite, γ-CEHC (i.e., chromanol ring without the farnesol tail; see FIG. 2) is the same metabolite for gamma-T3 and for gamma-T1. Such a metabolite has also been identified for alpha-T1, as α-CEHC. Accordingly, the metabolite for delta-T3 and delta-T1, is δ-CEHC.

Cholesterol Biosynthesis

Some 80% of cholesterol in the human body is endogenously produced in the liver, and the remaining 20% from dietary sources. Physiological studies show that cholesterol biosynthesis is nocturnal when dietary intake is at its lowest. When statin is taken in the evening versus morning, lipids drop about 10% more (Wallace, A., et al., 2003). Tocotrienols taken with food more than double their absorption and their maximum concentrations peak 4-6 hours after the supplementation (Yap, S., et al., 2001; Fairus, S., et al., 2003).

Definitions

Annatto extract—A source of material known as a byproduct solution of *Bixa orellana* seed components, which is obtained as an oily oleoresinous material after the bulk of annatto color, is largely removed from either the aqueous extract or solvent extract of annatto seeds. Further, this byproduct contains a tocotrienol component and a geranyl geraniol component and can be used as a source for the recovery of a tocotrienol component and a geranyl geraniol component.

Annatto Extract Oil—The oily product from the annatto seed extract containing the tocotrienols and tocopherols, collectively tocochromanols (Vitamin E), which are in the 350-450 Dalton MW fraction of the extract. Vegetable cooking oils, commonly known as triglycerides, which have a range of molecular weights of 500-1000 Daltons, and are essentially free or free of tocotrienols and tocopherols (typically <0.05% Vitamin E) are not included within this definition.

Appropriate Spectrum of Tocols—Mixtures of annatto tocotrienols with other plant extracts to achieve efficacy of the newly constituted tocols composition. Annatto tocotrienols satisfy this definition by having the highest amount of C5 unsubstituted tocotrienols and the lowest amount of tocopherols, especially alpha-T1.

Chemotactic Bioactive Materials—Biochemical molecules involved in any oxidative/inflammatory process that leads to loss of arterial vasculature.

Corn Oil—The oily product from the corn extract containing the tocotrienols and tocopherols, collectively tocochromanols (Vitamin E), which are in the 350-450 Dalton MW fraction of the extract. Vegetable cooking oils, commonly known as triglycerides, which have a range of molecular weights of 500-1000 Daltons, and are essentially free or free of tocotrienols and tocopherols (typically <0.1% Vitamin E) are not included within this definition.

Cottonseed Oil—The oily product from the cottonseed extract containing the tocotrienols and tocopherols, collectively tocochromanols (Vitamin E), which are in the 350-450 Dalton MW fraction of the extract. Vegetable cooking oils, commonly known as triglycerides, which have a range of molecular weights of 500-1000 Daltons, and are essentially free or free of tocotrienols and tocopherols (typically <0.1% Vitamin E) are not included within this definition.

Cranberry Seed Oil—The oily product from the cranberry seed extract containing the tocotrienols and tocopherols, collectively tocochromanols (Vitamin E), which are in the 350-450 Dalton MW fraction of the extract. Vegetable cooking oils, commonly known as triglycerides, which have a range of molecular weights of 500-1000 Daltons, and are essentially free or free of tocotrienols and tocopherols (typically <0.1% Vitamin E) are not included within this definition.

Essentially Free of Bixins—A composition that contains less than 0.1% by weight of bixins.

Litchi Seed Oil—The oily product from the litchi seed extract containing the tocotrienols and tocopherols, collectively tocochromanols (Vitamin E), which are in the 350-450 Dalton MW fraction of the extract. Vegetable cooking oils, commonly known as triglycerides, which have a range of molecular weights of 500-1000 Daltons, and are essentially free or free of tocotrienols and tocopherols (typically <0.1% Vitamin E) are not included within this definition.

MW (Molecular Weight) Fraction—Refers to the part (fraction) of a substance (i.e., natural extract) that has chemicals of that molecular weight. A standard analytical tool in Biochemistry or Chemistry is the separation of a substance into its various individual chemicals by their molecular weight. Typical methods include column chromatography, HPLC, and SDS-PAGE. Each of these analytical tools will separate a complex substance (i.e., natural extract) so the individual chemicals will travel at different rates through the medium (e.g., silica or coated silica, sepharose beads or polymerized gels). In the case of column chromatography or HPLC, the carrier solution is collected (e.g., test tubes) as it comes off the column into "fractions". There is a detector on the end of the column which detects the presence of material. The detector charts the "peaks" and the corresponding fraction that contains this material. The molecular weights of these peaks can be calculated using standards with known molecular weights (e.g., Keyhole Limpet Hemocyanin) or the pure compounds with previously identified MWs.

Natural Extract—Nonsynthetic (natural). A substance that is derived from mineral, plant, or animal matter and does not undergo a synthetic process as defined in section 6502(21) of 7 U.S.C. 6502(21) (the Act). For the purposes of this part, nonsynthetic is used as a synonym for natural as the term is used in the Act. [(21) Synthetic: The term "synthetic" means a substance that is formulated or manufactured by a chemical process or by a process that chemically changes a substance extracted from naturally occurring plant, animal, or mineral sources, except that such term shall not apply to substances created by naturally occurring biological processes.]

Oat Bran Oil—The oily product from the oat bran extract containing the tocotrienols and tocopherols, collectively tocochromanols (Vitamin E), which are in the 350-450 Dalton MW fraction of the extract. Vegetable cooking oils, commonly known as triglycerides, which have a range of molecular weights of 500-1000 Daltons, and are essentially free or free of tocotrienols and tocopherols (typically <0.1% Vitamin E) are not included within this definition.

Olive Oil—The oily product from the olive extract containing the tocotrienols and tocopherols, collectively tocochromanols (Vitamin E), which are in the 350-450 Dalton MW fraction of the extract. Vegetable cooking oils, commonly known as triglycerides, which have a range of molecular weights of 500-1000 Daltons, and are essentially free or free of tocotrienols and tocopherols (typically <0.1% Vitamin E) are not included within this definition.

Palm Oil—The oily product from the palm extract containing the tocotrienols and tocopherols, collectively tocochromanols (Vitamin E), which are in the 350-450 Dalton MW fraction of the extract. Vegetable cooking oils, commonly known as triglycerides, which have a range of molecular weights of 500-1000 Daltons, and are essentially free or free of tocotrienols and tocopherols (typically <0.1% Vitamin E) are not included within this definition.

Purification of Annatto Extract—A process to obtain isomers of tocotrienol and geranylgeraniol where the ratios are different from found in nature.

Purified Annatto Geranylgeraniol Composition—A composition purified from an annatto extract that contains one or more of the isomers of geranylgeraniol in a ratio that is different from the natural ratio found in an annatto extract.

Purified Annatto Tocotrienol Composition—A composition purified from an annatto extract that contains one or more of the isomers of tocotrienol in a ratio that is different from the natural ratio found in an annatto extract.

Rice Bran Oil—The oily product from the rice bran extract containing the tocotrienols and tocopherols, collectively tocochromanols (Vitamin E), which are in the 350-450 Dalton MW fraction of the extract. Vegetable cooking oils, commonly known as triglycerides, which have a range of molecular weights of 500-1000 Daltons, and are essentially free or free of tocotrienols and tocopherols (typically <0.1% Vitamin E) are not included within this definition.

Soy Oil—The oily product from the soybean extract containing the tocotrienols and tocopherols, collectively tocochromanols (Vitamin E), which are in the 350-450 Dalton MW fraction of the extract. Vegetable cooking oils, commonly known as triglycerides, which have a range of molecular weights of 500-1000 Daltons, and are essentially free or free of tocotrienols and tocopherols (typically <0.1% Vitamin E) are not included within this definition.

Sunflower Seed Oil—The oily product from the sunflower seed extract containing the tocotrienols and tocopherols, collectively tocochromanols (Vitamin E), which are in the 350-450 Dalton MW fraction of the extract. Vegetable cooking oils, commonly known as triglycerides, which have a range of molecular weights of 500-1000 Daltons, and are essentially free or free of tocotrienols and tocopherols (typically <0.1% Vitamin E) are not included within this definition.

Tocols—A general term for tocotrienols, tocopherols, tocochromanols, vitamin Es, mixed tocopherols and tocotrienols, TRFs including any additionally separated/fractionated forms, admixtures of annatto tocotrienols and other plant-derived TRFs, appropriate spectrum tocols, admixture of annatto tocotrienols with other tocols in order to standardize the amount and type of tocotrienols and/or tocopherols and the amount or ratio of alpha-tocopherol or other tocopherols present in the admixture.

Tocopherol—A chromanol with any degree of substitution with a saturated phytyl tail. Substitution in the chromanol is taken to mean any adduct of the alcohol and/or the ring moiety.

Tocopherol-Free—A preparation of tocotrienols and the tocotrienols are predominantly delta-T3 and/or gamma-T3 where the tocopherols are <0.5%.

Tocotrienol—A chromanol with any degree of substitution with an unsaturated tail of 1 to 3 double bonds. Substitution in the chromanol is taken to mean any adduct of the alcohol and/or the ring moiety.

Wheat Germ Oil—The oily product from the wheat germ extract containing the tocotrienols and tocopherols, collectively tocochromanols (Vitamin E), which are in the 350-450 Dalton MW fraction of the extract. Vegetable cooking oils, commonly known as triglycerides, which have a range of molecular weights of 500-1000 Daltons, and are essentially

SUMMARY OF THE INVENTION

The invention relates to a composition comprising annatto extract [350-450 Dalton molecular weight fraction] containing tocotrienol. Additionally, the invention relates to a composition where the tocotrienol includes all the chemically synthesized forms of delta-tocotrienol and gamma-tocotrienol, such as, DL-delta-tocotrienol and DL-gamma-tocotrienol.

In one embodiment the invention is drawn to a composition where the delta-to-gamma ratio of tocotrienols is between 1:100 to 100:1. In a preferred embodiment the invention is drawn to a composition where the delta-to-gamma ratio of tocotrienols is between 1:25 to 25:1. In a more preferred embodiment the invention is drawn to a composition of where the delta-to-gamma ratio of tocotrienols is between 1:10 to 10:1. In a more preferred embodiment the invention is drawn to a composition where the delta-to-gamma ratio of tocotrienols is between 1:5 to 5:1. In a more preferred embodiment the invention is drawn to a composition where the delta-to-gamma ratio of tocotrienols is 1:1.

In one embodiment the invention is drawn to a composition of tocotrienols comprising a mixture of an annatto extract [350-450 Dalton molecular weight fraction] and a 350-450 Dalton molecular weight fraction of a natural extract where the mixture has standardized low levels of tocopherols. In a preferred embodiment the invention is drawn to a composition where the standardized level of tocopherols is ≤50%. In a more preferred embodiment the invention is drawn to a composition where the standardized level of tocopherols is ≤20%. In a more preferred embodiment the invention is drawn to a composition where the standardized level of tocopherols is ≤10%. In a most preferred embodiment the invention is drawn to a composition where the standardized level of tocopherols is ≤1%. In another embodiment the invention is drawn to a composition of tocotrienols where the natural extract [350-450 Dalton molecular weight fraction] is selected from the group consisting of oils from rice bran, palm, cranberry seed, and litchi seed.

In another embodiment the invention is drawn to a composition comprising an annatto extract [350-450 Dalton molecular weight fraction] containing tocopherol, where the tocopherol is alpha-T1. In a preferred embodiment the invention is drawn to a composition comprising an annatto extract [350-450 Dalton molecular weight fraction] containing tocopherol, where the amount of the alpha-T1 is ≤50% of the total tocopherols. In a more preferred embodiment the invention is drawn to a composition comprising an annatto extract [350-450 Dalton molecular weight fraction] containing tocopherol, where the amount of the alpha-T1 is ≤25% of the total tocopherols. In a more preferred embodiment the invention is drawn to a composition comprising an annatto extract [350-450 Dalton molecular weight fraction] containing tocopherol, where the amount of the alpha-T1 is ≤10% of the total tocopherols. In a most preferred embodiment the invention is drawn to a composition comprising an annatto extract [350-450 Dalton molecular weight fraction] containing tocopherol, where the amount of the alpha-T1 is ≤1% of the total tocopherols.

In one embodiment the invention is drawn to a composition comprising a mixture of annatto extract [350-450 Dalton molecular weight fraction] and a 350-450 Dalton molecular weight fraction of a natural extract that is an appropriate spectrum. In a preferred embodiment the invention is drawn to a composition where ≥50% of the tocotrienols are delta-T3 and gamma-T3. In a more preferred embodiment the invention is drawn to a composition where ≥50% of the tocotrienols are delta-T3. In a most preferred embodiment the invention is drawn to a composition where it is tocopherol-free.

In one embodiment the invention is drawn to a composition where the C5 unsubstituted tocotrienols are ≥60%, and tocopherols are ≤15%. In a preferred embodiment the invention is drawn to a composition where the C5 unsubstituted tocotrienols are ≥70% C5 unsubstituted tocotrienols and ≤10% tocopherols. In a more preferred one embodiment the invention is drawn to a composition where the C5 unsubstituted tocotrienols are ≥80% C5 unsubstituted tocotrienols and ≤5% tocopherols.

In one embodiment the invention is drawn to a composition comprising annatto extract [350-450 Dalton molecular weight fraction], where blood level of triglyceride decreases. In a preferred embodiment the invention is drawn to a composition comprising annatto extract [350-450 Dalton molecular weight fraction], where the decrease in the blood level of the triglyceride has an effect selected from the group consisting of reversal of insulin resistance, metabolic syndrome, prediabetes, diabetes and diabetes-related cardiovascular disease.

In one embodiment the invention is drawn to a method to reverse insulin resistance, comprising administering annatto extract [350-450 Dalton molecular weight fraction] containing tocotrienols and potentiating insulin. In a more preferred embodiment the invention is drawn to a method lowering the risk of a disease selected from the group consisting of CVD, T2DM, hypertension, PCOS and fatty liver disease.

In one embodiment the invention is drawn to a composition comprising annatto extract [350-450 Dalton molecular weight fraction] where the tocotrienols lower CRP. In a preferred embodiment the invention is drawn to a composition comprising annatto extract [350-450 Dalton molecular weight fraction] where the tocotrienols lower CRP and protect against inflammation. In a more preferred embodiment the invention is drawn to a composition comprising annatto extract [350-450 Dalton molecular weight fraction] where the tocotrienols elevate HDL. In a more preferred embodiment the invention is drawn to a composition comprising annatto extract [350-450 Dalton molecular weight fraction] where the tocotrienols lower cholesterol and decrease cardiovascular risk index. In a more preferred embodiment the invention is drawn to a composition comprising annatto extract [350-450 Dalton molecular weight fraction] where the tocotrienols lower cholesterol and metabolic risk index.

In one embodiment the invention is drawn to a composition comprising annatto extract [350-450 Dalton molecular weight fraction] where the composition is tocopherol-free with ≥98% tocotrienols, and tocotrienols are predominantly delta-T3 and gamma-T3. In a more preferred embodiment the invention is drawn to a composition where the composition is tocopherol-free with ≥98% tocotrienols and tocotrienols are predominantly delta-T3.

In one embodiment the invention is drawn to a composition comprising annatto extract [350-450 Dalton molecular weight fraction] where the composition produces beneficial effects listed in Tables 2 & 4. In a preferred embodiment the invention is drawn to a composition comprising annatto extract [350-450 Dalton molecular weight fraction] where C5 unsubstituted tocols produce the beneficial effects in Tables 2 & 4.

TABLE 4

Appropriate spectrum tocols based on annatto tocols and/or admixture applications.*

| Conditions and Diseases | Tocotrienols, Tocopherols or Admixtures |
|---|---|
| Oxidation | Annatto, Soy and Rice |
| Inflammation, natriuresis/hypertension | Annatto alone |
| | Soy alone |
| Cholesterol, skin damage, | Annatto alone |
| hypertension, osteoporosis | Annatto and Palm |
| | Annatto and Rice |
| Cancer | Annatto alone |
| Dyslipidemia, hypertriglyceridemia | Annatto alone |
| Bioavailability | Annatto alone |
| | Annatto and Soy |
| | Soy alone |
| Inflammation, endocrinal and | Annatto alone |
| chemotactic, bioactive materials, | Annatto and Soy |
| hypercoagulation, vasculature loss | Soy alone |
| Insulin dysfunction & resistance | Annatto alone |
| | Annatto and Soy |
| | Soy alone |
| Brain/nerve damage and aging | Annatto alone |
| | Annatto and Soy |
| | Soy alone |
| Glycoxidation/HbA1c/AGE, SREBP-1 and FFA/TG, PPAR($\gamma$, $\alpha$, $\delta$) and IR, diabetes, hypertension | Annatto alone |
| Life extension, immunity enhancement | Annatto alone |
| | Annatto and palm |

*Tocol mixtures is intended to produce the highest potency for the corresponding condition. See text for definition of "appropriate spectrum".

In one embodiment the invention is drawn to a composition comprising annatto extract [350-450 Dalton molecular weight fraction] where the tocopherol-free annatto tocotrienols, delta-T3 and gamma-T3, lower lipids. In a preferred embodiment the invention is drawn to a composition comprising annatto extract [350-450 Dalton molecular weight fraction] where the tocopherol-free annatto tocotrienols, delta-T3 and gamma-T3, lower lipids, particularly triglycerides. In a more preferred embodiment the invention is drawn to a composition comprising annatto extract [350-450 Dalton molecular weight fraction] where the tocopherol-free annatto tocotrienols, delta-T3 and gamma-T3, lower lipids, particularly triglycerides and do not cause a drop in CoQ10 level. In a more preferred embodiment the invention is drawn to a composition comprising annatto extract [350-450 Dalton molecular weight fraction] where the tocopherol-free annatto tocotrienols, delta-T3 and gamma-T3, lower lipids, particularly triglycerides, and cause an increase in CoQ10 level. In a more preferred embodiment, the invention is drawn to a composition comprising annatto extract [350-450 Dalton molecular weight fraction] where the tocopherol-free annatto tocotrienols, delta-T3 and gamma-T3, lower lipids, particularly triglycerides, and cause an increase in CoQ10 level up to 20%. In a more preferred embodiment, the invention is drawn to a composition comprising annatto extract [350-450 Dalton molecular weight fraction] where the tocopherol-free annatto tocotrienols, delta-T3 and gamma-T3, lower lipids, particularly triglycerides, and cause an increase in CoQ10 level more than 20%.

In one embodiment the invention is drawn to a composition comprising annatto extract [350-450 Dalton molecular weight fraction] where the tocopherol-free annatto tocotrienols, delta-T3 and gamma-T3, lower lipids, particularly triglycerides, in normal weight, overweight and obese subjects. In a preferred embodiment the invention is drawn to a composition comprising annatto extract [350-450 Dalton molecular weight fraction] where the tocopherol-free annatto tocotrienols, delta-T3 and gamma-T3, lower lipids, particularly triglycerides, in animals of both sexes. In a more preferred embodiment the invention is drawn to a composition comprising annatto extract [350-450 Dalton molecular weight fraction] where the tocopherol-free annatto tocotrienols, delta-T3 and gamma-T3, lower lipids, particularly triglycerides, in humans of both sexes.

In one embodiment the invention is drawn to a method comprising administering annatto extract [350-450 Dalton molecular weight fraction] where the dose of tocopherol-free annatto tocotrienols, delta-T3 and gamma-T3, is given in a range from 10 to 1000 mg per day. In a preferred embodiment the invention is drawn to a method comprising administering annatto extract [350-450 Dalton molecular weight fraction] where the dose of tocopherol-free annatto tocotrienols, delta-T3 and gamma-T3, is given in a range from 20 to 500 mg per day. In a more preferred embodiment the invention is drawn to a method comprising administering annatto extract [350-450 Dalton molecular weight fraction] where the dose of tocopherol-free annatto tocotrienols, delta-T3 and gamma-T3, is given in a range from 50 to 150 mg per day.

In one embodiment the invention is drawn to a composition comprising annatto extract [350-450 Dalton molecular weight fraction] where the annatto C5 unsubstituted tocotrienols potentiate insulin to promote insulin sensitivity and reverse insulin resistance. In a preferred embodiment the invention is drawn to a composition comprising annatto extract [350-450 Dalton molecular weight fraction] where the annatto C5 unsubstituted tocotrienols potentiate insulin to promote insulin sensitivity and reverse insulin resistance with supplementation of varying duration. In a more preferred embodiment the invention is drawn to a composition comprising annatto extract [350-450 Dalton molecular weight fraction] where the annatto C5 unsubstituted tocotrienols potentiate insulin to promote insulin sensitivity and reverse insulin resistance with supplementation in normal weight, overweight, and obese subjects. In a more preferred embodiment the invention is drawn to a composition comprising annatto extract [350-450 Dalton molecular weight fraction] where the annatto C5 unsubstituted tocotrienols potentiate insulin to promote insulin sensitivity and reverse insulin resistance with supplementation in animals of both sexes. In a more preferred embodiment the invention is drawn to a composition comprising annatto extract [350-450 Dalton molecular weight fraction] where the tocopherol-free annatto tocotrienols, delta-T3 and gamma-T3, lower lipids, particularly triglycerides, in humans of both sexes.

In one embodiment the invention is drawn to a composition comprising annatto extract [350-450 Dalton molecular weight fraction] where the annatto tocotrienols reverse insulin resistance and potentiating insulin. In a preferred embodiment the invention is drawn to a composition comprising annatto extract [350-450 Dalton molecular weight fraction] where the annatto tocotrienols reverse insulin resistance and potentiating insulin, and lower the risk of a disease selected from the group consisting of CVD, T2DM, hypertension, PCOS and fatty liver disease. In a more preferred embodiment the invention is drawn to a composition comprising annatto extract [350-450 Dalton molecular weight fraction] where the annatto tocotrienols reverse insulin resistance and potentiating insulin, and reduce conditions in prediabetic and diabetes patients.

In one embodiment the invention is drawn to a composition comprising annatto extract [350-450 Dalton molecular weight fraction] where C5 unsubstituted tocols inhibit surface chemotactic bioactive materials (CBM). In a preferred embodiment the invention is drawn to a composition comprising annatto extract [350-450 Dalton molecular weight fraction] where annatto C5 unsubstituted T3 inhibit surface chemotactic bioactive materials. In a more preferred embodiment the invention is drawn to a composition comprising annatto extract [350-450 Dalton molecular weight fraction] where annatto C5 unsubstituted T3 inhibit surface chemotactic bioactive materials and prevent the tether or adhesion of circulating monocytes and leucocytes onto stationary endothelia. In a more preferred embodiment the invention is drawn to a composition comprising annatto extract [350-450 Dalton molecular weight fraction] where annatto C5 unsubstituted T3 inhibit surface chemotactic bioactive materials and prevent the tether or adhesion of circulating monocytes and leucocytes onto stationary endothelia that cause the loss of vasculature integrity. In a more preferred embodiment the invention is drawn to a composition comprising annatto extract [350-450 Dalton molecular weight fraction] where annatto C5 unsubstituted T3 inhibit surface chemotactic bioactive materials and prevent the tether or adhesion of circulating monocytes and leucocytes onto stationary endothelia that cause the loss of vasculature integrity, and prevent micro- and macro-vascular diseases, and atherosclerosis. In a more preferred embodiment the invention is drawn to a composition comprising annatto extract [350-450 Dalton molecular weight fraction] where annatto C5 unsubstituted T3 inhibit CBM and prevent pathological events selected from the group consisting of chemotaxis, vasoconstriction, hypercoagulation, glycoxidation and oxidized LDL by via HDL elevation.

In one embodiment the invention is drawn to a method comprising administering annatto extract [350-450 Dalton molecular weight fraction] where the appropriate dose of the C5 unsubstituted tocols is low. In a preferred embodiment the invention is drawn to a method comprising administering annatto extract [350-450 Dalton molecular weight fraction] where the appropriate dose of the C5 unsubstituted tocols is low because delta-T3 and gamma-T3 interact synergistically. In a more preferred embodiment the invention is drawn to a method comprising administering annatto extract [350-450 Dalton molecular weight fraction] where the appropriate dose of the C5 unsubstituted tocols is low because delta-T3 and gamma-T3 interact synergistically, and alpha-T3 is absent. In a more preferred embodiment the invention is drawn to a method comprising administering annatto extract [350-450 Dalton molecular weight fraction] where the appropriate dose of the C5 unsubstituted tocols is low because of enhanced uptake/bioavailability of C5 unsubstituted annatto T3 facilitates all site-specific PPAR activation. In a more preferred embodiment the invention is drawn to a method comprising administering annatto extract [350-450 Dalton molecular weight fraction] where the appropriate dose of the C5 unsubstituted tocols is low because of enhanced uptake/bioavailability of C5 unsubstituted annatto T3 facilitates all site-specific PPAR activation and SREBP-1 deactivation.

In one embodiment the invention is drawn to a composition comprising annatto extract [350-450 Dalton molecular weight fraction] where PPAR activation and/or SREBP-1 deactivation is in an organ or tissue. In a preferred embodiment the invention is drawn to a composition comprising annatto extract [350-450 Dalton molecular weight fraction] where PPAR activation and SREBP-1 deactivation is in a site selected from the group consisting of adipose, liver and skeletal muscle.

In one embodiment the invention is drawn to a composition comprising annatto extract [350-450 Dalton molecular weight fraction] where the tocotrienols have efficient passage through cancer cells, neurons for nerve protection/repair, skin for protection/repair, liver for catabolism to CEHCs, and arterial wall for CBM inhibition and NOS induction.

In one embodiment the invention is drawn to a composition comprising annatto extract [350-450 Dalton molecular weight fraction] where SREBP-1 deactivation inhibit biosynthesis of fatty acid and decreases TG. In a preferred embodiment the invention is drawn to a composition comprising annatto extract [350-450 Dalton molecular weight fraction] where SREBP-1 deactivation inhibit biosynthesis of fatty acid and decreases TG in an organ or tissue. In a more preferred embodiment the invention is drawn to a composition comprising annatto extract [350-450 Dalton molecular weight fraction] where SREBP-1 deactivation inhibit biosynthesis of fatty acid and decreases TG in a site selected from the group consisting of adipose, liver and skeletal muscle.

In one embodiment the invention is drawn to a composition where C5 unsubstituted T3 activate the nuclear transcription factor PPAR (γ, α, δ, or mixed) expression. In a preferred embodiment the invention is drawn to a composition comprising annatto extract [350-450 Dalton molecular weight fraction] where C5 unsubstituted T3 activate the nuclear transcription factor PPAR (γ, α, δ, or mixed) expression. In a more preferred embodiment the invention is drawn to a composition comprising annatto extract [350-450 Dalton molecular weight fraction] where annatto T3 activate the nuclear transcription factor PPAR (γ, α, δ, or mixed) expression and produce a metabolism-affected increase of cellular/mitochondrial uptake and beta-oxidation catabolism. In a more preferred embodiment the invention is drawn to a composition comprising annatto extract [350-450 Dalton molecular weight fraction] where annatto T3 activate the nuclear transcription factor PPAR (γ, α, δ, or mixed) expression and produce a metabolism-affected increase of cellular/mitochondrial uptake and beta-oxidation catabolism, and increase triglyceride metabolism. In a more preferred embodiment the invention is drawn to a composition comprising annatto extract [350-450 Dalton molecular weight fraction] where annatto T3 activate the nuclear transcription factor PPAR (γ, α, δ, or mixed) expression and produce a metabolism-affected increase of cellular/mitochondrial uptake and beta-oxidation catabolism, and increase triglyceride metabolism and decrease plasma FFA and triglyceride. In a more preferred embodiment the invention is drawn to a composition comprising annatto extract [350-450 Dalton molecular weight fraction] where annatto T3 activate the nuclear transcription factor PPAR (γ, α, δ, or mixed) expression and produce a metabolism-affected increase of cellular/mitochondrial uptake and beta-oxidation catabolism, and increase triglyceride metabolism, and decrease plasma FFA and triglyceride, which causes a reduction of hyperglycemia and HI, enhancement of IS and/or lowering of IR states.

In one embodiment the invention is drawn to a composition comprising annatto extract [350-450 Dalton molecular weight fraction] where SREBP-1 deactivation and PPAR activation by T3 control the synthesis and metabolism of FFA/TG. In a preferred embodiment the invention is drawn to a composition comprising annatto extract [350-450 Dalton molecular weight fraction] where SREBP-1 deactivation and PPAR activation by T3 control the synthesis and metabolism of FFA/TG and cause decrease plasma lipids, reduce fat storage and/or weight loss.

In one embodiment the invention is drawn to a composition comprising annatto extract [350-450 Dalton molecular weight fraction] where C5 unsubstituted tocols reverse nerve damage, decrease hypertension, enhance immunity, prevent osteoporosis, inhibit cancer, and repair skin damage. In a preferred embodiment the invention is drawn to a composition comprising annatto extract [350-450 Dalton molecular weight fraction] where C5 unsubstituted tocotrienols, reverse nerve damage, decrease hypertension, enhance immunity, prevent osteoporosis, inhibit cancer, and repair skin damage. In a more preferred embodiment the invention is drawn to a composition comprising annatto extract [350-450 Dalton molecular weight fraction] where annatto tocotrienols reverse nerve damage, decrease hypertension, enhance immunity, prevent osteoporosis, inhibit cancer, and repair skin damage.

In one embodiment the invention is drawn to a composition comprising annatto extract [350-450 Dalton molecular weight fraction] where the tocotrienols are diluted and added in glycerides. In a preferred embodiment the invention is drawn to a composition comprising annatto extract [350-450 Dalton molecular weight fraction] where the tocotrienols are diluted and added in glycerides, such as, stable tocotrienol-containing triglycerides. In a more preferred embodiment the invention is drawn to a composition comprising annatto extract [350-450 Dalton molecular weight fraction] where the tocotrienols are diluted and added in glycerides, such as, stable tocotrienol-containing triglycerides selected from the group consisting of rice bran, oat bran, palm, olive, wheat germ, cranberry seed, and litchi seed.

In one embodiment the invention is drawn to a composition comprising annatto extract [350-450 Dalton molecular weight fraction] where the tocotrienols are diluted, and added in glycerides and phospholipids. In a preferred embodiment the invention is drawn to a composition comprising annatto extract [350-450 Dalton molecular weight fraction] where the tocotrienols are diluted, and added in glycerides and phospholipids selected from the group consisting of lecithin, phosphatidyl choline/serine. In a more preferred embodiment the invention is drawn to a composition comprising annatto extract [350-450 Dalton molecular weight fraction] where the tocotrienols are diluted and added in glycerides and phospholipids, and contain high levels of nutrient-rich non-saponifiables.

In one embodiment the invention is drawn to a method to enhance absorption, where tocotrienols are taken at night. In a preferred embodiment the invention is drawn to a method to enhance absorption where tocotrienols are taken from 5 pm to midnight. In a more preferred embodiment the invention is drawn to a method to enhance absorption where tocotrienols are taken within 2 hours after dinner time. In a more preferred embodiment the invention is drawn to a method to enhance absorption where tocotrienols are taken from 7 pm to 10 pm. In a more preferred embodiment the invention is drawn to a method to enhance absorption where tocotrienols are taken at night to suppress cholesterol biosynthesis. In a more preferred embodiment the invention is drawn to a method to enhance absorption where tocopherols are taken in the morning. In a more preferred embodiment the invention is drawn to a method to enhance absorption where tocopherols are taken in the morning, and the tocopherols are alpha-T1. In a more preferred embodiment the invention is drawn to a method to enhance absorption where tocopherols are taken farthest in time from the tocotrienol consumption. In a more preferred embodiment the invention is drawn to a method to enhance absorption where tocopherols are taken 10-14 hours from the time tocotrienols are taken.

In one embodiment the invention is drawn to a composition comprising annatto extract [350-450 Dalton molecular weight fraction] where the annatto extract [350-450 Dalton molecular weight fraction] is administered to humans, mammals, avians, fish, crustaceans, and domestic and farm animals. In an additional embodiment the invention is drawn to a composition comprising annatto extract [350-450 Dalton molecular weight fraction] where the annatto extract [350-450 Dalton molecular weight fraction] has pharmaceutical, medical, and veterinary applications.

In one embodiment the invention is drawn to a composition comprising annatto extract [350-450 Dalton molecular weight fraction] where annatto extract [350-450 Dalton molecular weight fraction] is combined with other nutrients. In a preferred embodiment the invention is drawn to a composition comprising annatto extract [350-450 Dalton molecular weight fraction] where annatto extract [350-450 Dalton molecular weight fraction] is combined with other nutrients, and the annatto extract [350-450 Dalton molecular weight fraction] contains tocotrienol and geranyl geraniol. In a more preferred embodiment the invention is drawn to a composition comprising annatto extract [350-450 Dalton molecular weight fraction] where the nutrient is selected from the group consisting of phytosterols, oryzanols, policosanols, pantethine, red yeast rice (Monascus), oat bran, garlic, gugul lipids, chitosan, soy protein (e.g., oligo- and poly-peptides, hydrolysates), CoQ10, carnitine, magnesium, calcium, D-tyrosine, fibers (insoluble and soluble types, including beta-glucans), omega-3s (DHAs and EPAs, ALAs), and phospholipids (lecithins, phosphotidyl compounds of choline, serine, inositol, ethanolamine).

In an another embodiment the invention is drawn to a composition comprising annatto extract [350-450 Dalton molecular weight fraction] where the nutrient is selected from the group consisting of banaba extract (e.g., corosolic acid), lipoic acids (all isomeric forms), chromium, and the B vitamins including niacin.

In one embodiment the invention is drawn to a composition comprising annatto extract [350-450 Dalton molecular weight fraction] where annatto extract [350-450 Dalton molecular weight fraction] is combined with other nutrients, and the annatto extract [350-450 Dalton molecular weight fraction] contains tocotrienol and geranyl geraniol, and the formulation effects heart, brain, nerve, vascular, diabetes, and metabolic syndromes. In a preferred embodiment the invention is drawn to a composition comprising annatto extract [350-450 Dalton molecular weight fraction] where annatto extract [350-450 Dalton molecular weight fraction] is combined with other nutrients, and the annatto extract [350-450 Dalton molecular weight fraction] contains tocotrienol and geranyl geraniol, and the formulation effects the glucose-fatty acid cycle where glucose and fatty acid are reduced.

In one embodiment the invention is drawn to a composition where annatto extract [350-450 Dalton molecular weight fraction] is combined with a drug. In a preferred embodiment the invention is drawn to a composition comprising annatto extract [350-450 Dalton molecular weight fraction] where annatto extract [350-450 Dalton molecular weight fraction] is combined with a drug, and the drug is selected from the group consisting of lipid reducer, statin, inflammation reducer, COX 1 inhibitor, COX 2 inhibitor, anti-diabetic drug, TZD and fibrate. In a more preferred embodiment the invention is drawn to a composition comprising annatto extract [350-450 Dalton molecular weight fraction] where annatto extract [350-450 Dalton molecular weight fraction] is combined with a drug, and the annatto extract [350-450 Dalton molecular weight fraction] contains tocotrienol and geranyl geraniol.

DETAILED DESCRIPTION OF THE INVENTION AND PREFERRED EMBODIMENT

Detailed Description of the Preferred Embodiment

Figure 1:
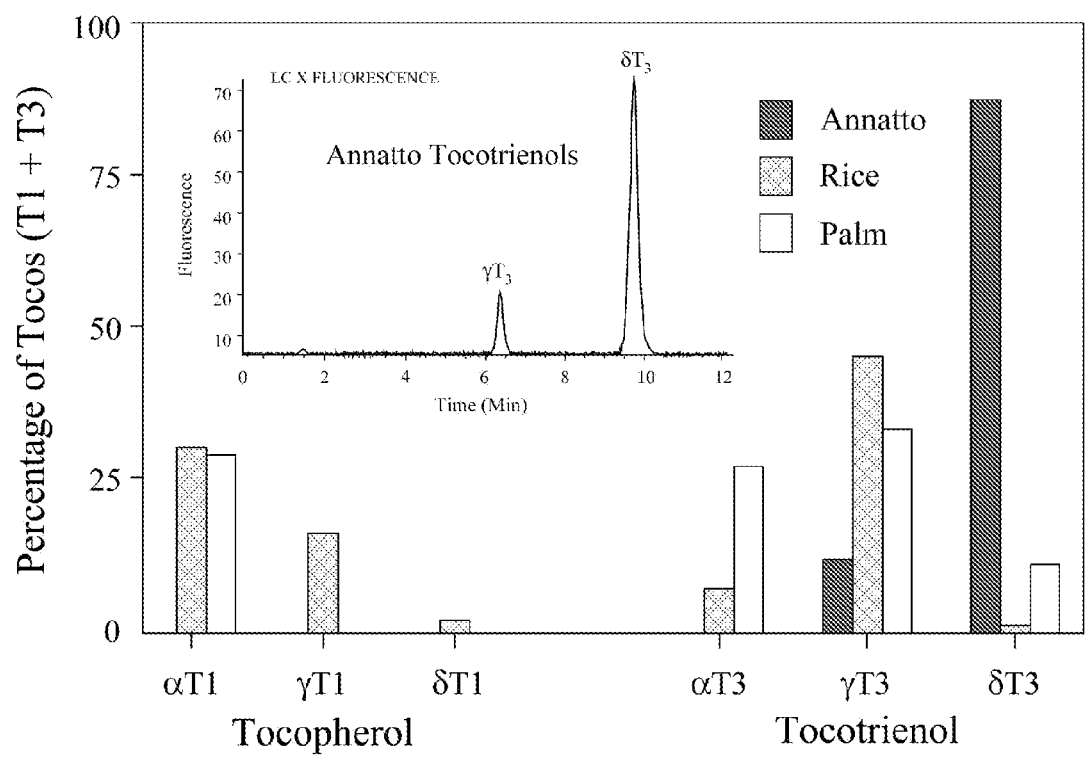
FIG. 1 illustrates the comparison of available plant-derived tocotrienols-containing products with a HPLC insert of annatto tocotrienols.
Figure 2:
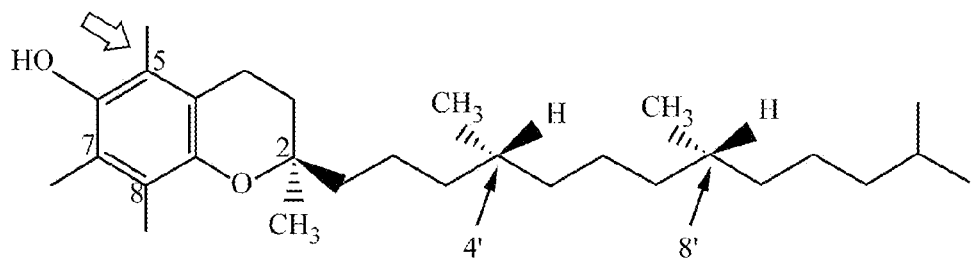
FIG. 2 illustrates natural vitamin E tocochromanols, highlighting the carbon-5 unsubstituted (hollow arrows) tocols and geranyl geraniol moiety.
Figure 2:
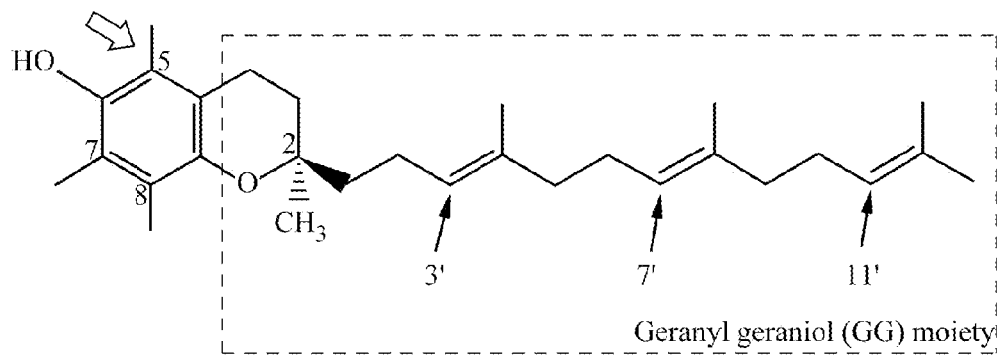

In one embodiment a composition contains annatto extract [350-450 Dalton molecular weight fraction] with tocotrienol. In a preferred embodiment the composition contains annatto extract [350-450 Dalton molecular weight fraction] with tocotrienol, where the tocotrienol can be all the chemically synthesized forms of delta-tocotrienol and gamma-tocotrienol, such as, DL-delta-tocotrienol and DL-gamma-tocotrienol.

In one embodiment a composition contains annatto extract [350-450 Dalton molecular weight fraction] with tocotrienol, where the tocotrienol contains delta-tocotrienol and gamma-tocotrienol, and where the delta-to-gamma ratio of tocotrienols is between 1:100 to 100:1. In a preferred embodiment the composition contains annatto extract [350-450 Dalton molecular weight fraction] with tocotrienol, where the tocotrienol contains delta-tocotrienol and gamma-tocotrienol, and where the delta-to-gamma ratio of tocotrienols is between 1:25 to 25:1. In a more preferred embodiment the composition contains annatto extract [350-450 Dalton molecular weight fraction] with tocotrienol, where the tocotrienol contains delta-tocotrienol and gamma-tocotrienol, and where the delta-to-gamma ratio of tocotrienols is between 1:10 to 10:1. In a more preferred embodiment the composition contains annatto extract [350-450 Dalton molecular weight fraction] with tocotrienol, where the tocotrienol contains delta-tocotrienol and gamma-tocotrienol, and where the delta-to-gamma ratio of tocotrienols is between 1:5 to 5:1. In a more preferred embodiment the composition contains annatto extract [350-450 Dalton molecular weight fraction] with tocotrienol, where the tocotrienol contains delta-tocotrienol and gamma-tocotrienol, and where the delta-to-gamma ratio of tocotrienols is 1:1.

In one embodiment a composition contains tocotrienol, where the composition is a mixture of an annatto extract [350-450 Dalton molecular weight fraction] and a 350-450 Dalton molecular weight fraction of a natural extract, and where the mixture has standardized low levels of tocopherols. In a preferred embodiment the composition contains tocotrienol, where the composition is a mixture of an annatto extract [350-450 Dalton molecular weight fraction] and a 350-450 Dalton molecular weight fraction of a natural extract, and where the standardized level of tocopherols is ≤50%. In a more preferred embodiment the composition contains tocotrienol, where the composition is a mixture of an annatto extract [350-450 Dalton molecular weight fraction] and a 350-450 Dalton molecular weight fraction of a natural extract, and where the standardized level of tocopherols is ≤20%. In a more preferred embodiment the composition contains tocotrienol, where the composition is a mixture of an annatto extract [350-450 Dalton molecular weight fraction] and a 350-450 Dalton molecular weight fraction of a natural extract, and where the standardized level of tocopherols is ≤10%. In a more preferred embodiment the composition contains tocotrienol, where the composition is a mixture of an annatto extract [350-450 Dalton molecular weight fraction] and a 350-450 Dalton molecular weight fraction of a natural extract, and where the standardized level of tocopherols is ≤1%. In more preferred embodiment the composition contains tocotrienols, where the natural extract [350-450 Dalton molecular weight fraction] is selected from the group consisting of oils from rice bran, palm, cranberry seed, and litchi seed.

In one embodiment a composition contains tocopherol and the tocopherol is alpha-T1. In a preferred embodiment the composition contains alpha-T1, and the amount of the alpha-T1 is ≤50% of the total tocopherols. In a more preferred embodiment the composition contains alpha-T1, and the amount of the alpha-T1 is ≤25% of the total tocopherols. In a more preferred embodiment the composition contains alpha-T1, and the amount of the alpha-T1 is ≤10% of the total tocopherols. In a more preferred embodiment the composition contains alpha-T1, and the amount of the alpha-T1 is ≤1% of the total tocopherols.

In one embodiment a composition contains a mixture of annatto extract [350-450 Dalton molecular weight fraction] and a 350-450 Dalton molecular weight fraction of a natural extract that is an appropriate spectrum. In a preferred embodiment the composition contains a mixture of annatto extract [350-450 Dalton molecular weight fraction] and a 350-450 Dalton molecular weight fraction of a natural extract, and ≥50% of the tocotrienols are delta-T3 and gamma-T3. In a more preferred embodiment the composition contains a mixture of annatto extract [350-450 Dalton molecular weight fraction] and a 350-450 Dalton molecular weight fraction of a natural extract, and ≥50% of the tocotrienols are delta-T3. In a most preferred embodiment the composition contains a mixture of annatto extract [350-450 Dalton molecular weight fraction] and a 350-450 Dalton molecular weight fraction of a natural extract, and it is tocopherol-free.

In one embodiment a composition contains ≥60% C5 unsubstituted tocotrienols and ≤15% tocopherols. In a preferred embodiment a composition contains ≥70% C5 unsubstituted tocotrienols and ≤10% tocopherols. In a more preferred one embodiment a composition contains ≥80% C5 unsubstituted tocotrienols and ≤5% tocopherols.

In one embodiment a composition contains annatto extract [350-450 Dalton molecular weight fraction], and the annatto extract [350-450 Dalton molecular weight fraction] decreases blood level of triglyceride. In a preferred embodiment the composition contains annatto extract [350-450 Dalton molecular weight fraction], where the annatto extract [350-450 Dalton molecular weight fraction] contains tocotrienols, and the tocotrienol decreases blood level of triglyceride. In a more preferred embodiment the composition contains annatto extract [350-450 Dalton molecular weight fraction], where the annatto extract [350-450 Dalton molecular weight fraction] contains tocotrienols, and where the tocotrienol decreases blood level of triglyceride, and where the decrease in the blood level of the triglyceride has an effect selected from the group consisting of reversal of insulin resistance, metabolic syndrome, prediabetes, diabetes and diabetes-related cardiovascular disease.

In one embodiment a method to reverse insulin resistance, comprises administering annatto extract [350-450 Dalton molecular weight fraction] containing tocotrienols and potentiating insulin. In a preferred embodiment the method to reverse insulin resistance lowers the risk of a disease selected from the group consisting of CVD, T2DM, hypertension, PCOS and fatty liver disease.

In one embodiment a composition contains annatto extract [350-450 Dalton molecular weight fraction] and the tocotrienols lower CRP. In a preferred embodiment the composition contains annatto extract [350-450 Dalton molecular weight fraction], and the tocotrienols lower CRP and protect against inflammation. In a more preferred embodiment the composition contains annatto extract [350-450 Dalton molecular weight fraction] and the tocotrienols elevate HDL. In a more preferred embodiment the composition contains annatto extract [350-450 Dalton molecular weight fraction] and the tocotrienols lower cholesterol and decrease cardiovascular risk index. In a more preferred embodiment the composition contains annatto extract [350-450 Dalton molecular weight fraction] and the tocotrienols lower triglyceride and metabolic risk index.

In one embodiment a composition contains annatto extract [350-450 Dalton molecular weight fraction] and the composition is tocopherol-free with ≥98% tocotrienols, and tocotrienols are predominantly delta-T3 and gamma-T3. In a more preferred embodiment the composition contains annatto extract [350-450 Dalton molecular weight fraction] and is tocopherol-free with ≥98% tocotrienols and tocotrienols are predominantly delta-T3.

In one embodiment a composition contains annatto extract [350-450 Dalton molecular weight fraction] and the composition produces beneficial effects listed in Tables 2 & 4. In a preferred embodiment a composition contains a C5 tocol and the C5 unsubstituted tocol produces a beneficial effect in Tables 2 & 4.

In one embodiment a composition contains annatto extract [350-450 Dalton molecular weight fraction] and tocopherol-free annatto tocotrienols, and the tocopherol-free annatto tocotrienols lower lipids. In a preferred embodiment the composition contains annatto extract [350-450 Dalton molecular weight fraction] and tocopherol-free annatto tocotrienols, and the tocopherol-free annatto tocotrienols are delta-T3 and gamma-T3, where the delta-T3 and gamma-T3 lower lipids. In a more preferred embodiment the composition contains annatto extract [350-450 Dalton molecular weight fraction] and tocopherol-free annatto tocotrienols, and the tocopherol-free annatto tocotrienols are delta-T3 and gamma-T3, where the delta-T3 and gamma-T3 lower lipids, particularly triglycerides. In a more preferred embodiment the composition contains annatto extract [350-450 Dalton molecular weight fraction] and tocopherol-free annatto tocotrienols, and the tocopherol-free annatto tocotrienols are delta-T3 and gamma-T3, where the delta-T3 and gamma-T3 lower lipids, particularly triglycerides and do not cause a drop in CoQ10 level. In a more preferred embodiment the composition contains annatto extract [350-450 Dalton molecular weight fraction] and tocopherol-free annatto tocotrienols, and the tocopherol-free annatto tocotrienols are delta-T3 and gamma-T3, where the delta-T3 and gamma-T3 lower lipids, particularly triglycerides, and cause an increase in CoQ10 level. In a more preferred embodiment the composition contains annatto extract [350-450 Dalton molecular weight fraction] and tocopherol-free annatto tocotrienols, and the tocopherol-free annatto tocotrienols are delta-T3 and gamma-T3, where the delta-T3 and gamma-T3 lower lipids, particularly triglycerides, and cause an increase in CoQ10 level up to 20%. In a more preferred embodiment the composition contains annatto extract [350-450 Dalton molecular weight fraction] and tocopherol-free annatto tocotrienols, and the tocopherol-free annatto tocotrienols are delta-T3 and gamma-T3, where the delta-T3 and gamma-T3 lower lipids, particularly triglycerides, and cause an increase in CoQ10 level more than 20%.

In one embodiment a composition contains annatto extract [350-450 Dalton molecular weight fraction] and tocopherol-free annatto tocotrienols, and the tocopherol-free annatto tocotrienols are delta-T3 and gamma-T3, and where the delta-T3 and gamma-T3 lower lipids, particularly triglycerides, in normal weight, overweight and obese subjects. In a preferred embodiment the composition contains annatto extract [350-450 Dalton molecular weight fraction] and tocopherol-free annatto tocotrienols, and the tocopherol-free annatto tocotrienols are delta-T3 and gamma-T3, and where the delta-T3 and gamma-T3 lower lipids, particularly triglycerides, in animals of both sexes. In a more preferred embodiment the composition contains annatto extract [350-450 Dalton molecular weight fraction] and tocopherol-free annatto tocotrienols, and the tocopherol-free annatto tocotrienols are delta-T3 and gamma-T3, and where the delta-T3 and gamma-T3 lower lipids, particularly triglycerides, in humans of both sexes.

In one embodiment a method comprises administering annatto extract [350-450 Dalton molecular weight fraction] and tocopherol-free annatto tocotrienols, and the tocopherol-free annatto tocotrienols are delta-T3 and gamma-T3, is given in a range from 10 to 1000 mg per day. In a preferred embodiment a method comprises administering annatto extract [350-450 Dalton molecular weight fraction] and tocopherol-free annatto tocotrienols, and the tocopherol-free annatto tocotrienols are delta-T3 and gamma-T3, is given in a range from 20 to 500 mg per day. In a more preferred embodiment a method comprises administering annatto extract [350-450 Dalton molecular weight fraction] and tocopherol-free annatto tocotrienols, and the tocopherol-free annatto tocotrienols are delta-T3 and gamma-T3, is given in a range from 50 to 150 mg per day.

In one embodiment a composition contains annatto extract [350-450 Dalton molecular weight fraction] with tocotrienols and the annatto extract [350-450 Dalton molecular weight fraction] potentiates insulin and reverses insulin resistance. In a preferred embodiment a composition contains annatto extract [350-450 Dalton molecular weight fraction] with tocotrienols and the annatto extract [350-450 Dalton molecular weight fraction] potentiates insulin and reverses insulin resistance, and lower the risk of a disease selected from the group consisting of CVD, T2DM, hypertension, PCOS and fatty liver disease. In a more preferred embodiment a composition contains annatto extract [350-450 Dalton molecular weight fraction]with tocotrienols and the annatto extract [350-450 Dalton molecular weight fraction] potentiates insulin and reverses insulin resistance, and reduce conditions in prediabetic and diabetes patients.

In one embodiment a composition contains annatto extract [350-450 Dalton molecular weight fraction] with C5 unsubstituted tocotrienols, and the annatto extract [350-450 Dalton molecular weight fraction] potentiate insulin to promote insulin sensitivity and reverse insulin resistance. In a preferred embodiment a composition contains annatto extract [350-450 Dalton molecular weight fraction] with C5 unsubstituted tocotrienols, and the annatto extract [350-450 Dalton molecular weight fraction] potentiate insulin to promote insulin sensitivity and reverse insulin resistance with supplementation of varying duration. In a more preferred embodiment the composition contains annatto extract [350-450 Dalton molecular weight fraction] with C5 unsubstituted tocotrienols, and the annatto extract [350-450 Dalton molecular weight fraction] potentiate insulin to promote insulin sensitivity and reverse insulin resistance with supplementation in normal weight, overweight, and obese subjects. In a more preferred embodiment the composition contains annatto extract [350-450 Dalton molecular weight fraction] with C5 unsubstituted tocotrienols, and the annatto extract [350-450 Dalton molecular weight fraction] potentiate insulin to promote insulin sensitivity and reverse insulin resistance with supplementation in animals of both sexes. In a more preferred embodiment the composition contains annatto extract [350-450 Dalton molecular weight fraction] with C5 unsubstituted tocotrienols, and the annatto extract [350-450 Dalton molecular weight fraction] potentiate insulin to promote insulin sensitivity and reverse insulin resistance, in humans of both sexes.

In one embodiment a composition contains C5 unsubstituted tocols inhibit surface chemotactic bioactive materials. In a more preferred embodiment a composition contains C5 unsubstituted tocols, where the C5 unsubstituted tocols are C5 unsubstituted T3 and the C5 unsubstituted T3 inhibit surface chemotactic bioactive materials. In a more preferred embodiment a composition contains C5 unsubstituted tocols, where the C5 unsubstituted tocols are C5 unsubstituted T3 and the C5 unsubstituted T3 inhibit surface chemotactic bioactive materials and prevent the tether or adhesion of circulating monocytes and leucocytes onto stationary endothelia. In a more preferred embodiment a composition contains C5 unsubstituted tocols, where the C5 unsubstituted tocols are C5 unsubstituted T3 and the C5 unsubstituted T3 inhibit surface chemotactic bioactive materials and prevent the tether or adhesion of circulating monocytes and leucocytes onto stationary endothelia that cause the loss of vasculature integrity. In a more preferred embodiment a composition contains C5 unsubstituted tocols, where the C5 unsubstituted tocols are C5 unsubstituted T3 and the C5 unsubstituted T3 inhibit surface chemotactic bioactive materials and prevent the tether or adhesion of circulating monocytes and leucocytes onto stationary endothelia that cause the loss of vasculature integrity, and prevent micro- and macro-vascular diseases, and atherosclerosis. In a more preferred embodiment a composition contains C5 unsubstituted tocols, where the C5 unsubstituted tocols are C5 unsubstituted T3 and the C5 unsubstituted T3 inhibit surface chemotactic bioactive materials and prevent pathological events selected from the group consisting of chemotaxis, vasoconstriction, hypercoagulation, glycoxidation and oxidized LDL via HDL elevation.

In one embodiment a method comprises administering annatto extract [350-450 Dalton molecular weight fraction] C5 unsubstituted tocols, where the appropriate dose of the C5 unsubstituted tocols is low. In a preferred embodiment a method comprises administering annatto extract [350-450 Dalton molecular weight fraction] C5 unsubstituted tocols, where the appropriate dose of the C5 unsubstituted tocols is low because delta-T3 and gamma-T3 interact synergistically. In a more preferred embodiment a method comprises administering annatto extract [350-450 Dalton molecular weight fraction] C5 unsubstituted tocols, where the appropriate dose of the C5 unsubstituted tocols is low because of enhanced uptake/bioavailability of C5 unsubstituted annatto T3 facilitates all site-specific PPAR activation. In a more preferred embodiment a method comprises administering annatto extract [350-450 Dalton molecular weight fraction] C5 unsubstituted tocols, where the appropriate dose of the C5 unsubstituted tocols is low because of enhanced uptake/bioavailability of C5 unsubstituted annatto T3 facilitates all site-specific PPAR activation and SREBP-1 deactivation.

In one embodiment a composition contains annatto extract [350-450 Dalton molecular weight fraction] and C5 unsubstituted tocols, where PPAR activation and/or SREBP-1 deactivation is in an organ or tissue. In a preferred embodiment a composition contains annatto extract [350-450 Dalton molecular weight fraction] and C5 unsubstituted tocols, where PPAR activation and SREBP-1 deactivation is in a site selected from the group consisting of adipose, liver and skeletal muscle.

In one embodiment a composition contains annatto extract [350-450 Dalton molecular weight fraction] C5 unsubstituted tocols, and the tocotrienols have efficient passage through cancer cells for apoptosis, neurons for nerve protection/repair, skin for protection/repair, liver for catabolism to CEHCs, and arterial wall for CBM inhibition and NOS induction.

In one embodiment a composition contains annatto extract [350-450 Dalton molecular weight fraction], and the SREBP-1 deactivation inhibits biosynthesis of fatty acid and decreases TG. In a preferred embodiment a composition contains annatto extract [350-450 Dalton molecular weight fraction] and the SREBP-1 deactivation inhibits biosynthesis of fatty acid and decreases TG in an organ or tissue. In a more preferred embodiment a composition contains annatto extract [350-450 Dalton molecular weight fraction] and the SREBP-1 deactivation inhibits biosynthesis of fatty acid and decreases TG in a site selected from the group consisting of adipose, liver and skeletal muscle.

In one embodiment a composition contains C5 unsubstituted T3, where the C5 unsubstituted T3 activate the nuclear transcription factor PPAR ($\gamma$, $\alpha$, $\delta$, or mixed) expression. In a more preferred embodiment a composition contains C5 unsubstituted T3, where the C5 unsubstituted T3 activate the nuclear transcription factor PPAR ($\gamma$, $\alpha$, $\delta$, or mixed) expression and produce a metabolism-affected increase of cellular/mitochondrial uptake and beta-oxidation catabolism of fatty acid. In a more preferred embodiment a composition contains C5 unsubstituted T3, where the C5 unsubstituted T3 activate the nuclear transcription factor PPAR ($\gamma$, $\alpha$, $\delta$, or mixed) expression and produce a metabolism-affected increase of cellular/mitochondrial uptake and beta-oxidation catabolism of fatty acid, and increase triglyceride metabolism. In a more preferred embodiment a composition contains C5 unsubstituted T3, where the C5 unsubstituted T3 activate the nuclear transcription factor PPAR ($\gamma$, $\alpha$, $\delta$, or mixed) expression and produce a metabolism-affected increase of cellular/mitochondrial uptake and beta-oxidation catabolism of fatty acid, and increase triglyceride metabolism and decrease plasma FFA and triglyceride. In a more preferred embodiment a composition contains C5 unsubstituted T3, where the C5 unsubstituted T3 activate the nuclear transcription factor PPAR ($\gamma$, $\alpha$, $\delta$, or mixed) expression and produce a metabolism-affected increase of cellular/mitochondrial uptake and beta-oxidation catabolism of fatty acid, and increase triglyceride metabolism and decrease plasma FFA and triglyceride, which causes a reduction of hyperglycemia and HI, enhancement of IS and/or lowering of IR states.

In one embodiment a composition contains C5 unsubstituted T3, where C5 unsubstituted T3 causes SREBP-1 deactivation and PPAR activation, and control the synthesis and metabolism of FFA/TG. In a preferred embodiment a composition contains C5 unsubstituted T3, where C5 unsubstituted T3 causes SREBP-1 deactivation and PPAR activation, and control the synthesis and metabolism of FFA/TG and cause decrease plasma lipids, reduce fat storage and/or weight loss.

In one embodiment a composition contains a C5 unsubstituted tocol and the C5 unsubstituted tocol reverses nerve damage, decrease hypertension, enhance immunity, prevent osteoporosis, inhibit cancer, and repair skin damage. In a preferred embodiment a composition contains a C5 unsubstituted tocol and the C5 unsubstituted tocol is a C5 unsubstituted tocotrienol, and the C5 unsubstituted tocotrienol reverses nerve damage, decrease hypertension, enhance immunity, prevent osteoporosis, inhibit cancer, and repair skin damage. In a more preferred embodiment a composition contains a tocotrienol and the tocotrienol reverses nerve damage, decrease hypertension, enhance immunity, prevent osteoporosis, inhibit cancer, and repair skin damage.

In one embodiment a composition contains a tocotrienol, where the tocotrienols are diluted and added in a glyceride. In a preferred embodiment a composition contains a tocotrienol, where the tocotrienols are diluted and added in glycerides, such as, stable tocotrienol-containing triglycerides. In a more preferred embodiment a composition contains a tocotrienol, where the tocotrienols are diluted and added in glycerides, such as, stable tocotrienol-containing triglycerides selected from the group consisting of rice bran, oat bran, palm, olive, wheat germ, cranberry seed, and litchi seed.

In one embodiment a composition contains a tocotrienol, where the tocotrienols are diluted, and added in glycerides and phospholipids. In a more preferred embodiment a composition contains a tocotrienol, where the tocotrienols are diluted, and added in glycerides and phospholipids selected from the group consisting of lecithin, phosphatidyl choline/serine. In a more preferred embodiment a composition contains a tocotrienol, where the tocotrienols are diluted and added in glycerides and phospholipids, and contain high levels of nutrient-rich non-saponifiables.

In one embodiment a method to enhance absorption, comprises taking tocotrienols, where the tocotrienols are taken at night. In a preferred embodiment a method to enhance absorption, comprises taking tocotrienols, where the tocotrienols are taken from 5 pm to midnight. In a more preferred embodiment a method enhance absorption, comprises taking tocotrienols, where the tocotrienols are taken within 2 hours after dinner time. In a more preferred embodiment a method enhance absorption, comprises taking tocotrienols, where the tocotrienols are taken from 7 pm to 10 pm. In a more preferred embodiment a method enhance absorption, comprises taking tocotrienols, where the tocotrienols are taken at night to suppress cholesterol biosynthesis. In a more preferred embodiment a method to enhance absorption, comprises taking tocopherols, where tocopherols are taken in the morning. In a more preferred embodiment a method to enhance absorption, comprises taking tocopherols, where tocopherols are taken in the morning, and the tocopherols are alpha-T1. In a more preferred embodiment a method to enhance absorption, comprises taking tocopherols, where tocopherols are taken farthest in time from the tocotrienol consumption. In a more preferred embodiment a method to enhance absorption, comprises taking tocopherols, where tocopherols are taken 10-14 hours from the time tocotrienols are taken.

In one embodiment a composition contains annatto extract [350-450 Dalton molecular weight fraction], where annatto extract [350-450 Dalton molecular weight fraction] is administered to humans, mammals, avians, fish, crustaceans, and domestic and farm animals. In an additional embodiment a composition contains annatto extract [350-450 Dalton molecular weight fraction] where annatto extract [350-450 Dalton molecular weight fraction] has pharmaceutical, medical, and veterinary applications.

In one embodiment a composition contains annatto extract [350-450 Dalton molecular weight fraction] and the annatto extract [350-450 Dalton molecular weight fraction] is combined with other nutrients. In a preferred embodiment a composition contains annatto extract [350-450 Dalton molecular weight fraction] and the annatto extract [350-450 Dalton molecular weight fraction] is combined with other nutrients, and the annatto extract [350-450 Dalton molecular weight fraction] contains tocotrienol and geranyl geraniol. In a more preferred embodiment a composition contains annatto extracts and where the nutrient is selected from the group consisting of phytosterols, oryzanols, policosanols, pantethine, red yeast rice (Monascus), oat bran, garlic, gugul lipids, chitosan, soy protein (e.g., oligo- and poly-peptides, hydrolysates), CoQ10, carnitine, magnesium, calcium, D-tyrosine, fibers (insoluble and soluble types, including beta-glucans), omega-3s (DHAs and EPAs, ALAs), and phospholipids (lecithins, phosphotidyl compounds of choline, serine, inositol, ethanolamine). In an another embodiment a composition contains annatto extract [350-450 Dalton molecular weight fraction] and a nutrient, and the nutrient is selected from the group consisting of banaba extract (e.g., corosolic acid), lipoic acids (all isomeric forms), chromium, and the B vitamins including niacin.

In one embodiment a composition contains annatto extract [350-450 Dalton molecular weight fraction] and the annatto extract [350-450 Dalton molecular weight fraction] is combined with other nutrients, and the annatto extract [350-450 Dalton molecular weight fraction] contains tocotrienol and geranyl geraniol, and the formulation effects heart, brain, vascular, diabetes, and metabolic syndromes. In a preferred embodiment a composition contains annatto extract [350-450 Dalton molecular weight fraction] and the annatto extract [350-450 Dalton molecular weight fraction] is combined with other nutrients, and the annatto extract [350-450 Dalton molecular weight fraction] contains tocotrienol and geranyl geraniol, and the formulation effects the glucose-fatty acid cycle where glucose and fatty acid are reduced.

In one embodiment a composition contains annatto extract [350-450 Dalton molecular weight fraction] and the annatto extract [350-450 Dalton molecular weight fraction] is combined with a drug. In a preferred embodiment a composition contains annatto extracts and the annatto extract [350-450 Dalton molecular weight fraction] is combined with a drug, and the drug is selected from the group consisting of lipid reducer, statin, inflammation reducer, COX 1 inhibitor, COX 2 inhibitor, anti-diabetic drug, TZD and fibrate. In a more preferred embodiment a composition contains annatto extract [350-450 Dalton molecular weight fraction] and the annatto extract [350-450 Dalton molecular weight fraction] is combined with a drug, and the annatto extract [350-450 Dalton molecular weight fraction] contains tocotrienol and geranyl geraniol.

In one embodiment a composition contains annatto extract [350-450 Dalton molecular weight fraction], and the annatto extract [350-450 Dalton molecular weight fraction] has the highest amounts of C5 unsubstituted tocotrienols and the lowest amounts of tocopherols known of any plant source.

In one embodiment a composition contains annatto extract [350-450 Dalton molecular weight fraction], and the required tocotrienol dosage is about half that of other tocols mixtures for treatment. In a preferred embodiment a composition contains annatto extract [350-450 Dalton molecular weight fraction], and the required tocotrienol dosage is about half that of other tocols mixtures for treatment because of compositional efficacy and enhanced bioavailability to tissues.

In one embodiment a composition contains a rationalized efficacious admixture of annatto extract [350-450 Dalton molecular weight fraction] alone, or with other plant extracts where the amount of C5 unsubstituted tocotrienols is high and amounts of tocopherols is low.

In one embodiment a composition contains annatto extract [350-450 Dalton molecular weight fraction], where the amount of all C5 unsubstituted tocols (tocotrienols and tocopherols) is high to produce an "appropriate spectrum" tocol to target various conditions, diseases and organ sites, including cardiovascular and inflammatory diseases, prediabetic (insulin resistance and metabolic syndrome) and diabetic diseases, lipidemia and hypertriglyceridemia, arterial and vasculature dysfunction, and transcription factor regulation/expression (e.g., SREBP-1 deactivation and PPAR activation), skin and nerve damages/defects, osteoporosis, cancer, essential hypertension and low immunity.

In one embodiment a method uses essentially pure delta-tocotrienol (delta-T3) and gamma-tocotrienol (gamma-T3). In a preferred embodiment a method uses essentially pure delta-tocotrienol (delta-T3) and gamma-tocotrienol (gamma-T3) and mixes it with tocotrienol-rich-fractions (TRFs) from various sources that display biological and chemical activities.

In one embodiment a composition contains annatto extract [350-450 Dalton molecular weight fraction], and the lipid fraction contains high amounts of delta-T3 and lesser amounts of other tocotrienol(s).

In one embodiment a composition contains annatto extract [350-450 Dalton molecular weight fraction], and the annatto extract [350-450 Dalton molecular weight fraction] also contains varying amounts of geranyl geraniol, which work together with tocotrienols (because of their common moiety, farnesol) to normalize and/or modulate lipid metabolism among other benefits.

In one embodiment a composition contains annatto extract [350-450 Dalton molecular weight fraction] and tocotrienol, and the annatto extract [350-450 Dalton molecular weight fraction] is used alone or with varying amounts of tocotrienols and tocopherols derived from other natural extracts [350-450 Dalton molecular weight fraction], such as, but not limited to, soy, sunflower, cottonseed, corn, rice bran or palm oils.

In one embodiment a method mixes annatto-derived tocotrienols with other sources of tocopherols and tocotrienols to produce a product that contains substantial amounts of tocols that would produce a pharmacologic or interventional effect to target or treat various pathologic conditions or diseases.

In one embodiment a composition contains annatto extract [350-450 Dalton molecular weight fraction], and the annatto extract [350-450 Dalton molecular weight fraction] contains unadulterated annatto tocotrienols and it is essentially devoid of tocopherols, particularly for intervening diseases.

In one embodiment an appropriate spectrum composition contains an effective natural tocols extract [350-450 Dalton molecular weight fraction] containing ≥80% C5 unsubstituted tocols. In a preferred embodiment an appropriate spectrum composition contains an effective natural tocols extract [350-450 Dalton molecular weight fraction] containing ≥95% C5 unsubstituted tocols. In a more preferred embodiment an appropriate spectrum composition contains an effective natural tocols extract [350-450 Dalton molecular weight fraction] containing ≥95% C5 unsubstituted tocols, and contains primarily tocopherols and/or tocotrienols comprising of delta and gamma isomers.

In one embodiment an appropriate spectrum composition contains a mixture of tocotrienols that satisfies the definition, where in annatto tocotrienol is used alone, or a mixture of tocopherols, such as, soy tocopherols (as in soy extract [350-450 Dalton molecular weight fraction], without chemical methylation to alpha-T1) is used alone.

In one embodiment an appropriate spectrum composition contains mixtures of tocols, such as, a mixture of annatto and soy (to enhance all C5 unsubstituted tocols), annatto and palm (to enhance C5 unsubstituted T3), annatto and rice (to enhance C5 unsubstituted T3).

In one embodiment an appropriate spectrum composition contains annatto tocotrienols alone. In a preferred embodiment an appropriate spectrum composition is annatto tocotrienols alone, where the annatto tocotrienols have high amounts of C5 unsubstituted tocotrienols and have low amounts of tocopherols. In a more preferred embodiment an appropriate spectrum composition is annatto tocotrienols alone, where the annatto tocotrienols have high amounts of C5 unsubstituted tocotrienols and have low amounts of tocopherols, and the tocopherol is alpha-T1.

In one embodiment an appropriate spectrum composition with annatto tocols and extracts where the appropriate spectrum composition has applications described in Table 4.

In one embodiment TRF from palm and rice can be separated (e.g. chromatography) to fractionate or improve individual tocotrienols.

In one embodiment tocopherol-free and C5 unsubstituted tocotrienols can produce a beneficial effect selected from the group consisting of in reducing lipids, inhibiting cancers, retarding oxidation/glycoxidation, reversing insulin dysfunction/resistance, improving vascular function, reducing hypertension/natriuresis, reversing atherosclerosis/thrombosis, inhibiting inflammation, repairing CNS/nerve damage, improving bioavailability, managing sugar, protecting skin, increasing bone density, preventing osteoporosis, prolonging life, and boost immunity.

In one embodiment C5 unsubstituted tocopherols have efficient bioavailability. In a preferred embodiment C5 unsubstituted tocopherols, gamma-T1 and delta-T1 have more bioavailability than C5 substituted tocopherols.

In one embodiment C5 unsubstituted tocotrienols have efficient bioavailability. In a preferred embodiment C5 unsubstituted tocotrienols, gamma-T3 and delta-T3 have more bioavailability than C5 substituted tocotrienols.

In one embodiment annatto T3 has delta T3 and gamma T3 isomers and C-5 unsubstituted, and does not have alpha T3, tocopherols, and alpha T1.

In one embodiment annatto T3 lowers lipids and reverses insulin resistance.

In one embodiment annatto T3 lowers CRP. In a preferred embodiment annatto T3 lowers CRP and protects against inflammation.

In one embodiment annatto T3 lowers cholesterol. In a preferred embodiment annatto T3 lowers cholesterol and decreases cardiovascular risk index. In a more preferred embodiment annatto T3 lowers cholesterol, and decreases cardiovascular risk index and metabolic risk index.

In one embodiment annatto T3 lowers chemotaxis and bioactive materials in patients with atherosclerosis, prediabetes or diabetes.

In one embodiment a composition contains annatto T3, and the tocotrienols treat a malady effecting the central nervous system.

Other Embodiments

It is to be understood that while the invention has been described in conjunction with the detailed description thereof, the foregoing description is intended to illustrate and not limit the scope of the invention, which is defined by the scope of the appended claims. For example, although the above description relates to human cells, various aspects of the invention might also be applied to cells from other animals (e.g., mammals, avians, fish, crustaceans, and domestic and farm animals) by making appropriate modifications to the described methods. Other aspects, advantages, and modifications are within the scope of the following claims.

EXAMPLES

The following examples describe embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the example.

Example 1

Cholesterol

Table 5 shows the effect of annatto tocotrienol on lipidemic subjects and how it affected the drop of total cholesterol, LDL, and triglycerides, as well as, increasing HDL over each of the first 3 months and through 12 months. The duration of the study was designed to correspond to standard procedures for managing lipids effectively in just one month from supplementation and lasting indefinitely with continued usage. The annatto tocotrienol dose (about 50-100 mg per day) to reduce lipids was about two to three-fold less than other tocols materials (about 100-300 mg per day) typically from palm or rice TRFs. The significantly lower dose underscored the efficient bioavailability of the special C5 unsubstituted T3 unique to annatto extracts. The results were also applicable to C5 unsubstituted tocopherols, since gamma-T1 and delta-T1 are more bioavailable than C5 substituted tocopherols. Further, the lower dose of annatto tocotrienol in the human studies was due to a composite of other factors, specifically, it was a) mainly delta-T3 and gamma-T3, b) tocopherol-free, and c) delta-T3 and gamma-T3 behave synergistically. The TRFs in other sources contain large proportions of alpha-T3 which is the weakest (at least five-fold less active) cholesterol reducer and has no synergistic role with other tocotrienols. Also, the TRF in other sources contain large proportions of alpha T1 (25-50%) which antagonizes tocotrienol's ability to reduce cholesterol.

TABLE 5

Supplementation of annatto tocotrienols (75 mg per day) from 1 to 12 months on lipid reduction in lipidemic subjects.

| Lipid | 1-month study (2 patients) | 2-month study (5 patients) | 3-month study (3 patients) | 12-month study (2 patients) |
|---|---|---|---|---|
| Total C | 18.7% ↓ | 12.9% ↓ | 15.6% ↓ | 19.0% ↓ |
| HDL | 19.0% ↑ | 9.7% ↑ | — | — |
| LDL | 14.0% ↓ | 15.1% ↓ | 13.2% ↓ | 21.9% ↓ |
| Triglycerides | 19.6% ↓ | 21.3% ↓ | 30.5% ↓ | 8.6% ↓ |

Figure 3:
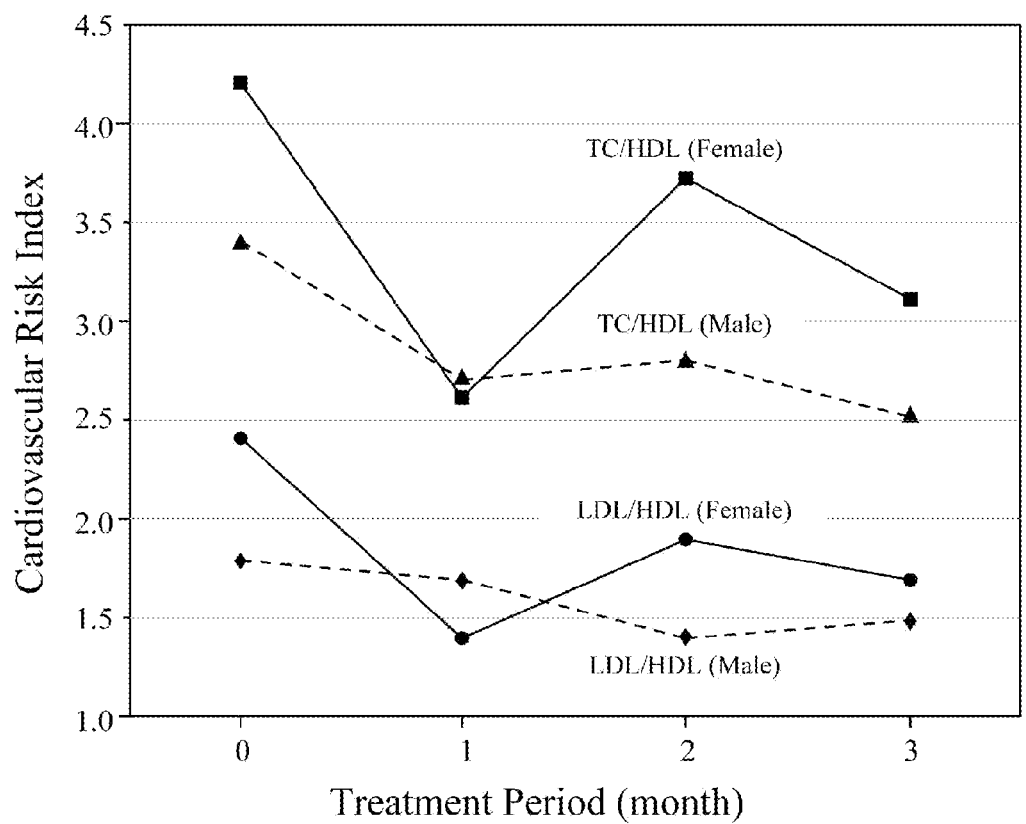
FIG. 3 illustrates the decrease of cardiovascular risk index in humans supplemented with annatto tocotrienols.

Unexpectedly, the triglycerides dropped (20-30%) in the first 3 months and represented the largest drop in triglyceride. The overall lipid management also underscored the uniqueness of annatto T3 to reduce cardiovascular risk. FIG. 3 shows the reduction in cardiovascular risk index (CRI) as indicated by the TC/HDL and LDL/HDL ratios. The CRI dropped with tocotrienol treatment, and further the reduction was seen in both sexes.

Table 6 compares the lipid management of normal weight and overweight/obese subjects. The cholesterol management (i.e., TC and LDL) improved in both groups and again triglycerides dropped in both groups. Generally, it is difficult to raise HDL in overweight subjects, and the increase in this group was modest (4%) compared to the normal weight group (10%). Nonetheless, the HDL increased with annatto tocotrienol supplementation. It was clearly documented that annatto extract [350-450 Dalton molecular weight fraction] tocotrienols effectively treated lipidemia of normal weight and overweight/obese subjects.

TABLE 6

Supplementation of annatto tocotrienols on normal weight and overweight/obese lipidemic subjects*.

| Subjects | TC (↓) | LDL (↓) | TG (↓) | HDL (↑) |
|---|---|---|---|---|
| Normal Weight | 13% | 15% | 21% | 10% |
| Overweight/Obese | 15% | 10% | 20% | 4% |

*Subjects are moderately hypercholesterolemic (ca 250 mg/dl). Each subject took 75 mg annatto tocotrienol per day for 2 months. Each group has 5 subjects.

Example 2

Insulin Resistance

The insulin resistance criteria were assessed on humans supplemented with annatto tocotrienol (Table 7). Both TG/HDL and TG dropped approximately 20-30% in normal weight subjects (2-month and 3-month studies) and in overweight/obese subjects (8-month study). Annatto C5 unsubstituted tocotrienols improved insulin sensitivity (IS) as evaluated by these two surrogate markers. Typically 4 of 5 subjects in each group had improved TG and TG/HDL, which showed improved insulin sensitivity. Also, 50% of the subjects in all groups (Table 7) that were previously IR prior to tocotrienol supplementation, based on the TG/HDL ratios, or about 20-40% reversal of IR back to IS if based on TG numbers, reversed back to IS.

TABLE 7

Human supplementation of annatto tocotrienols on improvement of insulin sensitivity and reversal of insulin resistance (IR)*

| Surrogate Marker | 2-month study (normal weight subjects) | 3-month study (normal weight subjects) | 8-month study (overweight/ obese subjects) |
|---|---|---|---|
| TG | 21.2% ↓ (1 in 5)@ | 27.9% ↓ (1 in 2) | 19.6% ↓ (2 in 5) |
| TG/HDL | 27.7% ↓ (2 in 4) | 28.0% ↓ (1 in 2) | 21.2% ↓ (1 in 2) |

*Each study group has 5 subjects, and each subject took 75 mg annatto tocotrienol per day.
@Using two IR surrogate markers (criteria; TG ≥ 140 mg/dl and/or TG/HDL ≥ 3.5), the number of subjects that reversed back to insulin sensitivity that were IR prior to tocotrienol supplementation.

For example, one human subject had a 43% drop in TG. The triglyceride level was 121 mg/dL before supplementation and decreased to 69 mg/dL 16 months after annatto T3 supplementation. Correspondingly, there was a 35% drop in TG/HDL ratio, and went from 1.86 before supplementation to 1.21 16 months after annatto T3 supplementation. Therefore, improvement in insulin action and reversal of IR is not temporary (Tables 5 and 6) and exceeded a year, and continued to stay down for 2.4 years. The duration of the study was designed to correspond to standard procedures for managing IR effectively in just one month from supplementation and lasting indefinitely with continued usage. Annatto C5 unsubstituted T3 potentiated IS and reversed IR in various study durations, in normal weight and overweight/obese subjects, and in both sexes. Furthermore, such insulin potentiation and IR reversal by annatto C5 unsubstituted T3 reduced the risk of CVD, T2DM, hypertension, PCOS and fatty liver disease.

Example 3

Inflammation

It was found that tocotrienols reduced C-reactive protein (CRP), a highly sensitive indicator or marker for inflammatory events leading to the progression of atherosclerosis and diabetes. CRP is a better responsive inflammation marker than cholesterol for cardiovascular risk and CRP predicts even low grade systemic inflammations that precede the development of T2DM.

Table 8 shows a 20-50% drop in CRP of subjects taking annatto tocotrienols. This represented the first time that tocotrienols (from any source) effectively reduced CRP. Tocotrienols reduced inflammation processes, which was responsible for a more effective reduction of atherosclerosis and thrombosis than previously envisioned when measured simply by cholesterol-associated lipids alone. The combined effect of annatto tocotrienols more effectively lowered lipids and inflammation processes, managed atherosclerosis and IR together, rather than just hypercholesterolemia by itself. Tocopherol was known to lower CRP to a comparable range to the present work (Table 8), but surprisingly, the required dosages of alpha-T1 are approximately 10-fold higher than that of annatto tocotrienols. This 10-fold potency of tocotrienols over tocopherol was due to the unique composition of C-5 unsubstituted tocotrienols.

TABLE 8

Human supplementation of annatto tocotrienols (75 mg per day) from 1 to 3 months on cardiovascular inflammation (C-reactive protein) reduction.

| Patient | 1 month | 2 month | 3 month |
|---|---|---|---|
| 1 | 57% ↓ | 50% ↓ | 50% ↓ |
| 2 | 42% ↓ | 42% ↓ | 53% ↓ |
| 3 | — | 24% ↓ | — |
| 4 | — | 21% ↓ | — |

There was a possible role of inflammatory proteins on the prediabetic condition, especially of IR, since people with IR have higher VCAM-1, CRP, IL-6 and TNFα. Since this study showed that annatto tocotrienols clearly lowered IR and CRP (Tables 7 and 8), it has been demonstrated that tocotrienols, especially C5 unsubstituted T3, help prevent diabetes and CVD (FIG. 3 and Table 5).

Example 4

Cardiovascular Disease

HDL increased (4-19%) in all subjects on annatto tocotrienol supplementation (Tables 5 and 6), indicating a reduction in cardiovascular risk. The supplementation even raised HDL in overweight subjects. Therefore, the annatto C5 unsubstituted T3, via increased HDL, exerted marked anti-inflammatory and anti-thrombotic effects independent of CRP, and inhibited/suppressed chemotactic bioactive materials (CBM) that tether circulating cells to arteries, inhibited LDL oxidation and NFkB activation.

Example 5

Lipidemia and Diabetic Dyslipidemia

Tables 5, 6 and 7 show that C5 unsubstituted T3 reduced IR and lipids (TG) in normal weight and overweight/obese subjects. C5 unsubstituted T3, in general, and annatto T3, in particular, deactivated the transcription factor SREBP-1 expression, and thereby inhibited the de novo synthesis of fatty acid and TG in various organs, including liver, adipose and skeletal muscle.

Example 6

Diabetes

Annatto C5 unsubstituted T3 retarded glycoxidation of lipids and proteins including AGE and HbA1c, and reversed microvascular diseases (e.g., kidney failure, peritonitis, retinopathy, polyneuropathy, peripheral atherosclerosis). C-5 unsubstituted tocols, in general, and annatto unsubstituted T3, in particular, specifically inhibited and reduced CBM.

Example 7

Peroxisomal Proliferator Activated Receptors

Tocotrienols, especially C5 unsubstituted annatto T3, are known to be more amenable to cellular uptake. Adipose, skin, liver and artery are major depots for tocotrienols. This site-specific T3 uptake is important because of the multiple tissue sites of all PPAR activation, and particularly important in adipose and liver tissues where PPARγ and PPARα are largely expressed. Additionally, the SREBP-1 expression in part controls FFA/TG synthesis, and PPAR expression in part controls FFA/TG uptake and catabolism. Therefore, the simultaneous SREBP-1 deactivation and PPAR activation by the C5 unsubstituted annatto T3 controlled FFA/TG regulation in concert with both the metabolism (anabolism and catabolism) and synthesis.

Example 8

Nervous System

A human subject recovering from stroke was unable to walk properly and had an unsteady gait. The subject received annatto T3 as a supplement. After supplementation with annatto T3 the subject was able to walk unaided and with balance. Observationally, the annatto T3 improved her autonomic nervous system.

The C5 unsubstituted tocols have unique bioavailability to cross the brain blood barrier as neuropotent agents to aid nerve growth, heal damaged nerves, and reverse chronic aging and/or acutely damaged brain.

Example 9

Statin Drugs

Although tocotrienols lowered cholesterol in the present study, they did not lower CoQ10. The endogenous CoQ10 increased about 20%, which suggested that tocotrienols, and particularly C-5 unsubstituted tocotrienols up regulated the liver's de novo synthesis of CoQ10.

Example 10

Topical Applications

A human subject with psoriasis on his palm received dietary annatto tocotrienols for one month. At the end of the month, his palm ceased to crack and bleed, and his psoriatic severity was reduced. A topical application of annatto tocotrienol for two weeks reduced the eczema on the finger of another human subject. At the end of this period, his finger ceased to itch and his parched skin was smoothened. After 4 weeks of treatment, he was healed of eczema. Annatto tocotrienol was uniquely suited for skin absorption and thereby reduced dermatological damages.

Example 11

Immune System

Experiments in these studies (using mostly C-5 unsubstituted tocols containing delta and gamma isomers) showed that annatto tocotrienols were uniquely suited for use to enhance the immune system.

Example 12

Bone Mineralization

Experiments in these studies (using mostly C-5 unsubstituted tocols containing delta and gamma isomers) showed that the unique tocopherol-free annatto tocotrienols promoted healthy bone mineralization and prevented osteoporosis.

Example 13

Hypertension

The administration of gamma-T3 prevented the development of increased blood pressure. Also, C-5 unsubstituted tocols (i.e., all delta and gamma isomers) had this effect. Gamma-T3, Delta-T3, and annatto tocotrienols reduced essential hypertension, increased NOS activity and produced the water-soluble catabolite natriuretic agents δ-CEHC and γ-CEHC.

Example 14

Cholesterol Biosynthesis

The peak plasma concentration of tocotrienols is correlated with the peak cholesterol biosynthesis by taking tocotrienols, especially annatto tocotrienols, at night preferably during or within 2 hours after dinner (e.g., 5 to 10 pm). Also, since the half life of alpha-T1 is longer than tocotrienols, supplementation of alpha-T1 (if it is taken or continued), is taken in the morning so it is the farthest from the tocotrienol consumption.

What is claimed is:

1. A composition comprising a mixture of an annatto extract with tocotrienol and a natural extract with tocotrienol, wherein the tocotrienol in the mixture has a ratio of delta-tocotrienol to gamma-tocotrienol from 1:25 to 25:1.

2. The composition of claim 1, wherein tocopherol is from less than 50% to less than 1%.

3. The composition of claim 1, where the natural extract is selected from the group consisting of soy, corn, rice bran, palm, olive, wheat germ, oat bran, sunflower seed, cottonseed, cranberry seed, and litchi seed.

4. The composition of claim 2, wherein the tocopherol is alpha-T1.

5. The composition of claim 1, wherein more than 50% of the tocotrienol is delta-T3 and gamma-T3.

6. The composition of claim 1, wherein more than 50% of the tocotrienol is delta-T3.

7. The composition of claim 1, wherein the composition is tocopherol-free.

8. The composition of claim 1, wherein the tocotrienol is a C5 unsubstituted tocotrienol and the composition comprises more than 60% C5 unsubstituted tocotrienol, and less than 15% tocopherol.

9. The composition of claim 1, wherein the tocotrienol activates PPARs.

10. The composition of claim 9, where the tocotrienol further down regulates SREBP transcription factors.

11. The composition of claim 1, where the tocotrienol decreases triglyceride concentration in blood.

12. The composition of claim 11, where the decrease in the triglyceride concentration in the blood has an effect selected from the group consisting of reversal of insulin resistance, metabolic syndrome, prediabetes, diabetes and diabetes-related cardiovascular disease.

13. The composition of claim 1, where a tocotrienol treats a malady affecting the central nervous system.

14. The composition of claim 13, where a tocotrienol treats a malady affecting the central nervous system, and the malady is selected from the group consisting of dysautonomia, acute nerve damage, neural degenerative genetic disease, acute brain damage, brain trauma, chronic nerve damage, neural toxicity, chronic brain damage, Alzheimer's, Parkinson's, and Huntington's.

15. The composition of claim 1, where the tocotrienol has a beneficial effect selected from the group consisting of lowers CRP, protects against inflammation, lowers cholesterol, decreases cardiovascular risk index, decreases metabolic risk index, decreases chemotactic bioactive materials, reduces osteoporosis, increases bone mineralization, enhances immune system, lowers lipids, and reverses insulin resistance.

* * * * *

UNITED STATES PATENT AND TRADEMARK OFFICE
CERTIFICATE OF CORRECTION

PATENT NO. : 8,586,109 B2  
APPLICATION NO. : 12/168819  
DATED : November 19, 2013  
INVENTOR(S) : Barrie Tan et al.

Page 1 of 2

It is certified that error appears in the above-identified patent and that said Letters Patent is hereby corrected as shown below:

Title Page, below Abstract "15 Claims, 3 Drawing Sheets" Should read---16 Claims, 3 Drawing Sheets (as shown on attached page)

In the Claims

Column 40, line 50 insert claim 16

--16. The composition of claim 1, further comprising a geranyl geraniol.--

Signed and Sealed this
Twenty-ninth Day of April, 2014

Michelle K. Lee
*Deputy Director of the United States Patent and Trademark Office*

(12) United States Patent
Tan et al.

(10) Patent No.: US 8,586,109 B2
(45) Date of Patent: Nov. 19, 2013

(54) ANNATTO EXTRACT COMPOSITIONS INCLUDING TOCOTRIENOLS AND TOCOPHEROLS AND METHODS OF USE

(75) Inventors: Barrie Tan, Amherst, MA (US); Jose Llobrera, Belchertown, MA (US)

(73) Assignee: American River Nutrition, Inc., Hadley, MA (US)

(*) Notice: Subject to any disclaimer, the term of this patent is extended or adjusted under 35 U.S.C. 154(b) by 817 days.

(21) Appl. No.: 12/168,819

(22) Filed: Jul. 7, 2008

(65) Prior Publication Data

US 2009/0041870 A1   Feb. 12, 2009

Related U.S. Application Data

(63) Continuation-in-part of application No. 10/823,043, filed on Apr. 12, 2004, now abandoned.

(60) Provisional application No. 60/488,310, filed on Jul. 18, 2003, provisional application No. 60/461,932, filed on Apr. 10, 2003.

(51) Int. Cl.
*A61K 36/185* (2006.01)

(52) U.S. Cl.
USPC .......... 424/727; 424/725; 424/764; 424/776; 424/750; 424/757

(58) Field of Classification Search
None
See application file for complete search history.

(56) References Cited

U.S. PATENT DOCUMENTS 5,157,132 A * 10/1992 Tan et al. ............. 549/413
6,350,453 B1 * 2/2002 Tan et al. ............. 424/776

FOREIGN PATENT DOCUMENTS

WO   03/013275 A1   2/2003

OTHER PUBLICATIONS

Frega et al., Identification and Estimation of Tocotrienols in the Annatto Liquid Fraction by Gas Chromatography-Mass Spectrum. 1998, JAOCS, 75: 1723-1727.*
Murray, 2003, http://www.lifeextensionvitamins.com/de2lcevic.html.*
Pearce et al., Hypocholesterolemic Activity of Synthetic and Natural Tocotrienols, 1992, J Med Chem, 35: 3595-3606.*
Office Action, dated May 24, 2011, Canadian Intellectual Property Office.
Morrision, Errol Y. St. A; West, Manley E., The effect of *Bixa orrellana* (annatto) on blood sugar levels in the anaesthetized dog. West Indian med. j; 34(1):38-42, Mar. 1985.
WM Wan Nazaimoon and BAK Khalid, Tocotrienols-rich diet decreases advanced glycosylation end-products in non-diabetic rats and improves glycemic control in streptozotocin-induced diabetic rats, vol. 24, No. 2 Dec. 2002, 77-82.
Canadian Office Action dated Aug. 20, 2013 corresponding to Application No. 2,521,020.

* cited by examiner

*Primary Examiner* — Terry McKelvey
*Assistant Examiner* — Catheryne Chen
(74) *Attorney, Agent, or Firm* — Hogan Lovells US LLP

(57) ABSTRACT

Compositions and methods of use of annatto extracts [350-450 Dalton molecular weight fraction] including tocotrienols and tocopherols with an appropriate spectrum. This spectrum includes but not limited to low alpha tocopherol, high delta- and gamma-tocols, and mixtures with other extracts [350-450 Dalton molecular weight fraction] like palm and rice and/or nutrients.

16 Claims, 3 Drawing Sheets